US008097446B2

(12) United States Patent
Lee et al.

(10) Patent No.: US 8,097,446 B2
(45) Date of Patent: Jan. 17, 2012

(54) *STAPHYLOCOCCUS AUREUS* STRAIN CYL1892

(75) Inventors: Chia Y. Lee, Little Rock, AR (US); Thanh T. Luong, Little Rock, AR (US)

(73) Assignee: Board of Trustees of the University of Arkansas, Little Rock, AR (US)

(*) Notice: Subject to any disclaimer, the term of this patent is extended or adjusted under 35 U.S.C. 154(b) by 169 days.

(21) Appl. No.: 12/398,821

(22) Filed: Mar. 5, 2009

(65) Prior Publication Data

US 2010/0184160 A1 Jul. 22, 2010

Related U.S. Application Data

(62) Division of application No. 11/285,700, filed on Nov. 21, 2005, now Pat. No. 7,521,221.

(51) Int. Cl.

| | |
|---|---|
| ***C12N 1/20*** | (2006.01) |
| ***C12N 15/64*** | (2006.01) |
| ***C12P 19/00*** | (2006.01) |
| ***C12P 19/04*** | (2006.01) |
| ***C12P 21/06*** | (2006.01) |
| ***G01N 33/569*** | (2006.01) |
| ***C07H 5/04*** | (2006.01) |
| ***C07H 21/04*** | (2006.01) |

(52) U.S. Cl. ...... 435/252.3; 435/72; 435/101; 435/69.1; 435/91.1; 435/7.33; 536/55.1; 536/23.7; 536/23.1

(58) Field of Classification Search ............... 435/252.3, 435/72, 101, 69.1, 91.1, 7.33; 536/55.1, 536/23.7, 23.1

See application file for complete search history.

(56) References Cited

U.S. PATENT DOCUMENTS

| | | | | |
|---|---|---|---|---|
| 5,843,780 | A | 12/1998 | Thomson | |
| 6,030,836 | A | 2/2000 | Thiede | |
| 6,200,806 | B1 | 3/2001 | Thomson | |
| 6,387,367 | B1 | 5/2002 | Davis-Sproul | |
| 6,800,480 | B1 | 10/2004 | Bodnar | |
| 6,911,201 | B1 | 6/2005 | Merchav | |
| 7,521,221 | B2 * | 4/2009 | Lee et al. | 435/252.3 |
| 2005/0013872 | A1 | 1/2005 | Freyman | |

FOREIGN PATENT DOCUMENTS

| | | | |
|---|---|---|---|
| WO | 2005009498 | | 2/2005 |
| WO | 2006114500 | A3 | 11/2006 |
| WO | 2007118979 | A1 | 10/2007 |

OTHER PUBLICATIONS

Luong et al., "Overproduction of Type 8 Capsular Polysaccharide Augments *Staphylococcus aureus* Virulence", Infection and Immunity, 2002, vol. 70, No. 7, pp. 3389-3395.

ISR for PCT/US08/51598 dated Aug. 15, 2008, 7 pages.

Sau et al., "The *Staphylococcus aureus* allelic genetic loci for serotype 5 and 8 capsule expression contain the type-specific genes flanked by common genes", Microbiology, 1997, vol. 143, pp. 2395-2405.

Sau et al., "Molecular Characterization and Transcriptional Analysis of Type 8 Capsule Genes in *Staphylococcus aureus*", Journal of Bacteriology, 1997, vol, 179, No. 5, pp. 1614-1621.

Tamama et al., "Epidermal Growth factor as candidate for ex vivo expansion of bone marrow-derived mesenchymal stem cells", Stem Cell Express, Sep. 8, 2005; pp. 1-40.

Oriordan et al, *Staphylococcus aureus* Capsular Polysaccharides, Clinical Microbiology Review, 2004, pp. 218-234, vol. 17, No. 1.

European Search Report for EP06846358 dated Mar. 9, 2009.

Abe, et al, Essential Requirement of BMPs2/4 for Both Osteoblast and Osteoclast Formation in Murine Bone Marrow Cultures from Adult Mice: Antagonism by Noggin, J. of Bone and Mineral Research, 2000, pp. 663-673, vol. 15, No. 4.

Baksh, et al, Adult mesenchymal stem cells: characterization, differentiation, and application in cell and gene therapy, J. Cell Mol. Med., 2004, pp. 301-316, vol. 8, No. 3.

Bi, et al, Extracellular Matrix Proteoglycans Control the Fate of Bone Marrow Stromal Cells, J. Biol Chem, 2005, pp. 30481-30489, vol. 280, No. 34.

Bianco, et al, Expression and Localization of the Two Small Proteoglycans Biglycan and Decorin in Developing Human Skeletal and Non-skeletal Tissues, J. Histrochemistry and Cytochemistry, 1990, pp. 1549-1563, vol. 38, No. 11.

Bianco, et al, Bone Marrow Stromal Stem Cells: Nature, Biology, and Potential Applications, Stem Cells, 2001, pp. 180-192, vol. 19.

Chen, et al, The small leucine-rich proteoglycan biglycan modulates BMP-4-induced osteoblast differentiation, FASEB J., 2004, pp. 948-958, vol. 18.

Chow, et al, Modeling pO2 Distributions in the Bone Marrow Hematopoietic Compartment. I. Krogh's Model, Biophysical J, 2001, pp. 675-684, vol. 81.

Dennis, et al, A Quadripotential Mesenchymal Progenitor Cell Isolated from the Marrow of an Adult Mouse, J Bone Miner Res, 1999, pp. 700-09, vol. 14, No. 5.

D'Ippolito, et al, Marrow-isolated adult multilineage inducible (MIAMI) cells, a unique population of postnatal young and old human cells with extensive expansion and differentiation potential, J. of Cell Science, 2004, pp. 2971-2981, vol. 117.

D'Ippolito, et al, Low oxygen tension inhibits osteogenic differentiation and enhances sternness of human MIAMI cells, Bone, 2006, pp. 513-22, vol. 39, No. 3.

Digregorio, et al, Attenuation of the self-renewal of transit-amplifying osteoblast progenitors in the murine bone marrow by 17B-estradiol, J. Clinical Investigation, 2001, pp. 803-812, vol. 107.

Engler, et al, Matrix Elasticity Directs Stem Cell Lineage Specification, Cell, 2006, pp. 677-689, vol. 126.

Gospodarowicz, et al, Comparison of the Ability of Basement Membranes Produced by Corneal Endothelial and Mouse-derived Endodermal PF-HR-9 Cells to Support the Proliferation and Differentiation of Bovine Kidney Tubule Epithelial Cells In Vitro, J. of Cell Biology, 1984, pp. 947-961, vol. 99.

Jiang, et al, Pluripotency of mesenchymal stern cells derived from adult marrow, Nature, 2002, pp. 41-49, vol. 418, No. 6893.

Katayama, et al, Signals from the Sympathetic Nervous System Regulate Hematopoietic Stem Cell Egress from Bone Marrow, Cell, 2006, pp. 407-421, vol. 124.

Klein,G., The extracellular matrix of the hematopoietic microenvironment, Experientia, 1995, pp. 914-926, vol. 51.

(Continued)

*Primary Examiner* — Ganapathirama Raghu

(57) ABSTRACT

This disclosure presents embodiments of novel strains of *Staphylococcus aureus* that through genetic engineering produce type 5 capsular polysaccharide at greater levels than *Staphylococcus aureus* strain Reynolds.

4 Claims, 6 Drawing Sheets

OTHER PUBLICATIONS

Krebsbach, et al, Bone Formation In Vivo: Comparison of Osteogenesis by Transplanted Mouse and Human Marrow Stromal Fibroblasts, Transplantation, 1997, pp. 1059-1069, vol. 63, No. 8.
Mizutani, et al, The Nature of Bone Morphogenetic Protein (BMP) Fractions Derived from Bovine Bone Matrix Gelatin, Clin. Orthop. Relat. Res., 1982, pp. 213-223, vol. 171.
Moriscot, et al, Human Bone Marrow Mesenchymal Stem Cells Can Express Insulin and Key Transcription Factors of the Endocrine Pancreas Developmental Pathway upon Genetic and/or Microenvironmental Manipulation In Vitro, Stem Cells, 2005, pp. 594-604, vol. 23.
Peister, et al, Adult stem cells from bone marrow (MSCs) isolated from different strains of inbred mice vary in surface epitopes, rates of proliferation, and differentiation potential, Blood, 2004, pp. 1662-1668, vol. 103, No. 5.
Sekiya, et al, Expansion of Human Adult Stem Cells from Bone Marrow Stroma: Conditions that Maximize the Yields of Early Progenitors and Evaluate Their Quality, Stem Cells, 2002, pp. 530-541, vol. 20.
Sethe, et al, Aging of mesenchymal stem cells, Ageing Res Rev, 2006, pp. 91-116, vol. 5, No. 1.
Grayson, et al, Human Mesenchymal Stem Cells Tissue Development in 3D PET Matrices, Biotechnol. Prog., 2004, pp. 905-912, vol. 20.
Sakai, et al, Transplantation of mesenchymal stem cells embedded in Atelocollagen gel to the intervertebral disc: a potential therapeutic model for disc degeneration, Biomaterials, 2003, pp. 3531-3541, vol. 24.
Tamama, et al, Epidermal Growth Factor as a Candidate for Ex Vivo Expansion of Bone Marrow-Derived Mesenchymal Stem Cells, Stem Cells, Mar. 2006, pp. 686-695, vol. 24, No. 3.
Higuchi, Using PCR to Engineer DNA, 1989, pp. 61-70, A. Erlich (ed.), PCR Technology, Stockton Press, New York, NY.
Sambrook, et al, Molecular Cloning: a Laboratory manual, 2nd ed., 1989, Cold Spring Harbor Laboratory, Cold Spring Harbor, NY.
European Examination Report dated Apr. 19, 2010 from related EP Application No. 06 846 358.7, 5 pgs.
Herbert S.; Regulation of *Staphylococcus aureus* Type 5 and Type 8 Capsular Polysaccharides by CO2; Journal of Bacteriology; Aug. 2001; p. 4609-4613.

* cited by examiner

PCR Primer Sequences

| | | |
|---|---|---|
| Ppa5ar1 | 5'-GGATCCCTTTTACCTGCACCAGGCTTTTC-3' | (SEQ ID NO:8) |
| Ppa5r2 | 5'-CCATGGCTCTAAAGTAGTAATAGTTTG-3' | (SEQ ID NO:9) |
| Ppa1r | 5'-TTCTAATGTACTTTCCATATAAACCTCCTATTTTCC-3' | (SEQ ID NO:10) |
| Ppa8af7 | 5'-AAATAGGAGGTTTATATGGAAAGTACATTAGAATTA-3' | (SEQ ID NO:11) |
| Ppa8f8 | 5'-GAATTCGAGTCTACAAGCGATTAAA-3' | (SEQ ID NO:12) |
| Ppa1fNcol | 5'-CGGCCATGGCCACAGTATAAATTATATCAG-3' | (SEQ ID NO:13) |

CYL1892

Reynolds

*STAPHYLOCOCUS AUREUS* STRAIN CYL1892

CROSS REFERENCE TO RELATED APPLICATION

This application is a divisional of U.S. Ser. No. 11/285,700, filed on Nov. 21, 2005, now U.S. Pat. No. 7,521,221, issued on Apr. 21, 2009, and is hereby incorporated by reference in its entirety.

REFERENCE TO "SEQUENCE LISTING" SUBMITTED ON CD

This specification is accompanied by an original compact disc and one identical copy, the contents of which are hereby incorporated by reference. The compact discs each contain the file: 5339-9952.txt.

BRIEF DESCRIPTION OF THE DRAWINGS

FIG. 1 illustrates the DNA sequences of primers utilized in various Polymerase Chain Reaction ("PCR") procedures for construction of a modified 5' control region for the cap5 operon of *Staphylococcus aureus* in which the cap1 promoter replaces the cap5 promoter. The DNA sequences are identified as SEQ ID NO:8, SEQ ID NO:9, SEQ ID NO:10, SEQ ID NO:11, SEQ ID NO:12, and SEQ ID NO:13.

FIG. 2A illustrates the location of PCR primers relative to the modified 5' control region DNA sequence. FIG. 2B illustrates the nature of the various DNA sequences of the modified 5' control region.

FIG. 4 illustrates the modified 5' control region integrated into the *Staphylococcus aureus* strain Reynolds genome to create a new strain of *Staphylococcus aureus* comprising a cap5 operon operably linked to a cap1 promoter.

FIG. 6 also illustrates the difference in type 5 capsular polysaccharide production between strain Reynolds and strain CYL 1982 when grown on solid media.

DESCRIPTION

Figure 2:
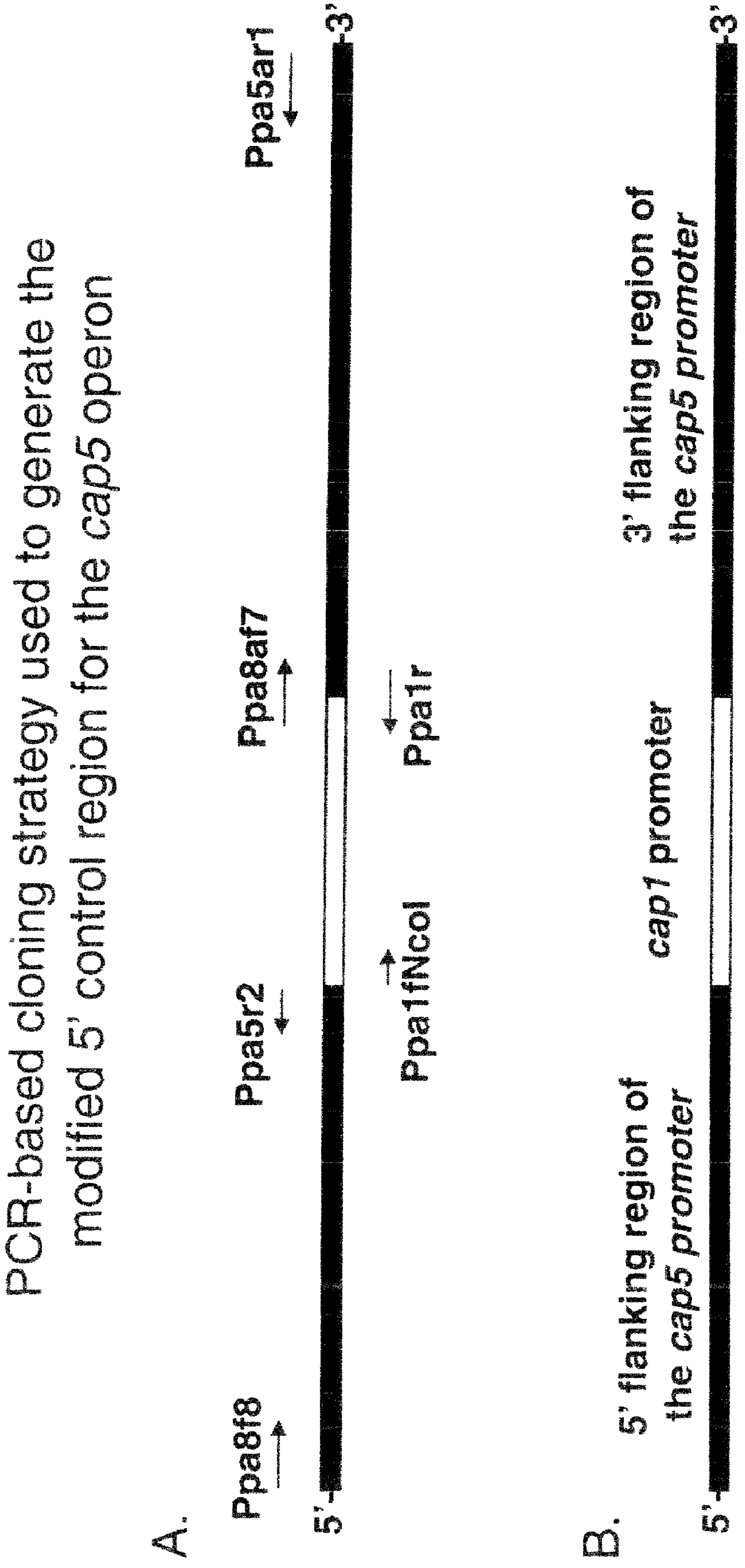
FIG. 2 illustrates the PCR-based cloning strategy utilized for replacing the cap5 promoter with the cap1 promoter. Specifically.
Figure 3:
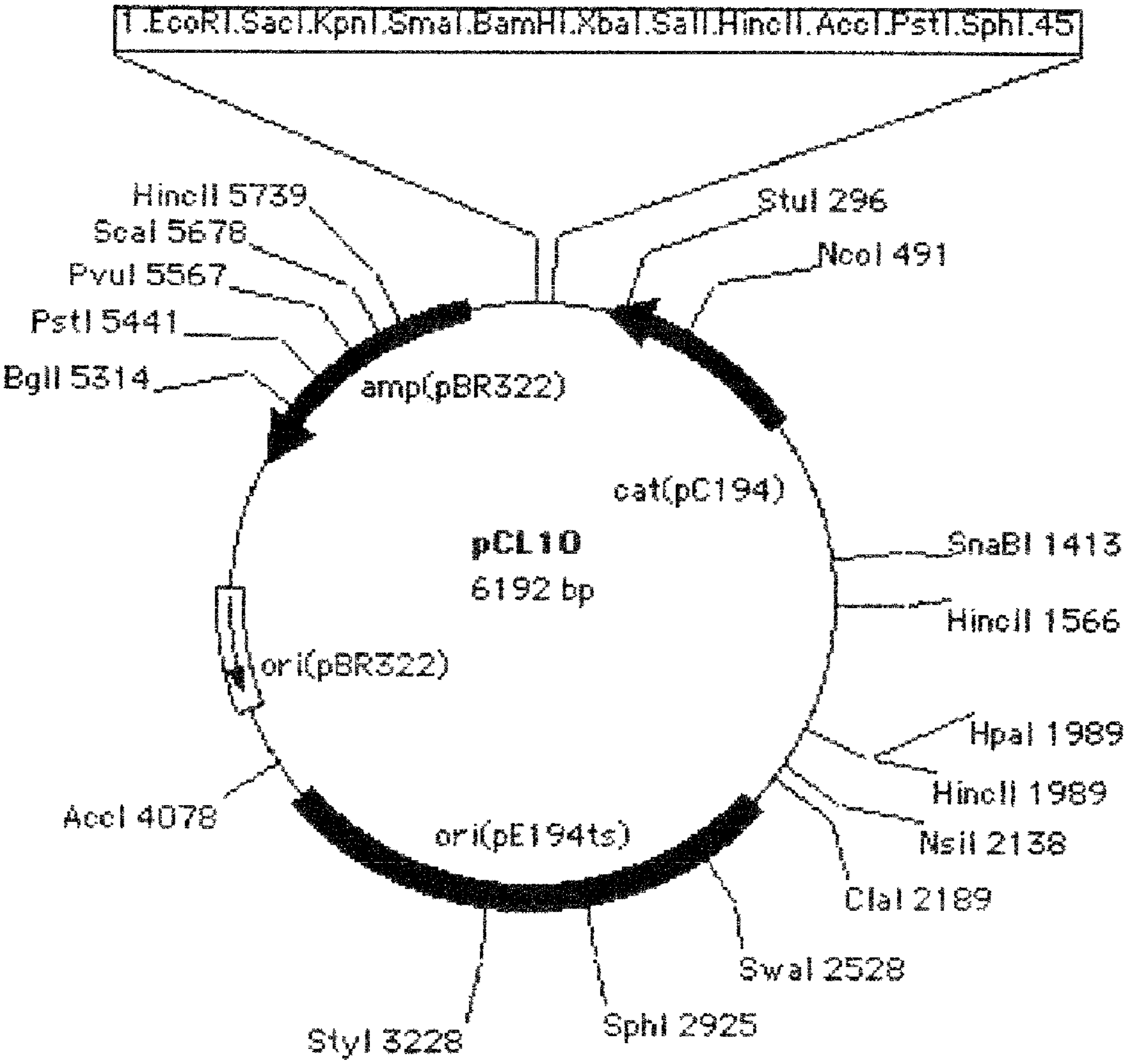
FIG. 3 illustrates a map of the shuttle vector pCL10 utilized in construction of the modified 5' control region for the cap5 operon.

This disclosure presents embodiments of novel strains of *Staphylococcus aureus* ("*S. aureus*") and uses thereof.

In various embodiments of the present invention, the cap5 operon of *S. aureus* is controlled by a constitutive promoter. In various embodiments of the present invention, said constitutive promoter is the cap1 promoter from *S. aureus* strain M. In various embodiments of the present invention, the strains of *S. aureus* encompassed by this disclosure produce type 5 capsular polysaccharide at greater levels than wild-type *S. aureus* strain Reynolds.

One embodiment of the present invention comprises CYL1892, a novel strain of *S. aureus*.

In one embodiment of the present invention, the cap5 operon comprises the genes cap5A through cap5P. In one embodiment of the present invention, the cap5 operon comprises the genes cap5A through cap5O. In various embodiments of the present invention, the cap5 operon comprises genes encoding proteins involved in the synthesis of type 5 capsular polysaccharide.

In various embodiments of the present invention, a method of producing type 5 capsular polysaccharide is disclosed wherein said method comprises culturing a strain of *S. aureus* encompassed by various embodiments of the present invention and obtaining type 5 capsular polysaccharide from the culture.

One embodiment of the present invention provides a deoxyribonucleic acid ("DNA") sequence comprising a 5' flanking region of the cap5 promoter linked to a cap1 promoter operably linked to a 3' flanking region of the cap5 promoter wherein said DNA sequence comprises a modified 5' control region. A promoter is operably linked to a DNA sequence if the promoter is joined to said DNA sequence in a manner capable of promoting transcription of the DNA sequence.

One embodiment of the present invention provides a DNA sequence comprising a modified 5' control region operably linked to a cap5 operon. Yet another embodiment provides a strain of *S. aureus* comprising a modified 5' control region operably linked to a cap5 operon wherein said strain of *S. aureus* produces approximately 11.5 fold more type 5 capsular polysaccharide than *S. aureus* strain Reynolds.

In various embodiments of the present invention, type 5 capsular polysaccharide comprises the structure→4)-β-D-ManNAcA(1→4)-α-L-FucNAc(3OAc)-(1→3)-β-D-FucNAc(1→.

In one embodiment of the present invention, the DNA primers listed in FIG. 1 may be utilized in Polymerase Chain Reactions to produce DNA sequences for construction of a constitutive promoter operably linked to a cap5 operon.

The forward primer Ppa8f8 (SEQ ID NO:12) and reverse primer Ppa5r2 (SEQ ID NO:9) are partially complementary to the genomic DNA of *S. aureus* strain Reynolds. PCR reactions using these primers and *S. aureus* strain Reynolds genomic DNA as template produce a 778 base pair ("bp") PCR product, SEQ ID NO:1. The PCR product identified as SEQ ID NO:1 comprises a DNA sequence that is substantially similar to a portion of the 5' flanking region of the cap5 operon of *S. aureus* strain Reynolds. The 5' flanking region of the cap5 operon is any sequence of DNA that is no more than about 10,000 bases, no more than about 5,000 bases, no more than about 4,000 bases, no more than about 3,000 bases, no more than about 2,000 bases, or no more than about 1,000 bases 5' to the cap5 promoter of the cap5 operon or DNA that is substantially similar to the 5' flanking region of the cap5 operon. Substantially similar DNA sequences are DNA sequences that have at least about 80% identity. While it is recognized that SEQ ID NO:1 was used in the construction of the modified 5' control region of one embodiment of the present invention, it is envisioned that other sequences of the 5' flanking region of the cap5 operon could be utilized to achieve substantially the same results in other embodiments. Therefore, the use of SEQ ID NO:1 should not be construed as limiting.

In various embodiments of the present invention, the cap5 promoter of the cap5 operon is replaced by a constitutive promoter. A constitutive promoter encompassed by embodiments of the present invention includes the cap1 promoter. It is envisioned that other constitutive promoters may be used in various embodiments of the present invention including, but not limited to, promoters that are substantially similar to the cap1 promoter. It is also envisioned that other sequences comprising the cap1 promoter may be used in various embodiments of the present invention. Therefore, the examples recited should not be construed as limiting the scope of the disclosure.

The promoter of the cap1 operon of *S. aureus* strain M is known to be a constitutive promoter. In one embodiment of the present invention, the cap5 promoter of *S. aureus* strain Reynolds has been replaced with the cap1 promoter of *S. aureus* strain M. The forward primer Ppa1fNcoI (SEQ ID NO:13) and reverse primer Ppa1r (SEQ ID NO:10) are partially complementary to the genomic DNA of *S. aureus* strain M. PCR using these primers and *S. aureus* strain M genomic DNA as template produces a 250 by PCR product, SEQ ID NO:2. In various embodiments of the present invention, the cap1 promoter of *S. aureus* strain M comprises the DNA sequence identified by SEQ ID NO:2.

In one embodiment of the present invention, a 3' flanking region of the cap5 promoter has been amplified by PCR. A 3' flanking region of the cap5 promoter may be a DNA sequence of the cap5 operon that is located 3' to the cap5 promoter including, but not limited to, any sequence comprising about the first 50 bases 3' to the cap5 promoter, about the first 100 bases 3' to the cap5 promoter, about the first 500 bases 3' to the cap5 promoter, about the first 1,000 bases 3' to the cap5 promoter, about the first 2,000 bases 3' to the cap5 promoter, about the first 5,000 bases 3' to the cap5 promoter, or about the first 10,000 bases 3' to the cap5 promoter or portions thereof.

PCR using the primers Ppa8af7 (SEQ ID NO:11) and Ppa5ar1 (SEQ ID NO:8) and *S. aureus* strain Reynolds genomic DNA as template produces an 872 bp PCR product that spans the cap5A gene and a partial cap5B gene. The 3' flanking region of the cap5 promoter comprises the 872 bp PCR product and is identified as SEQ ID NO:3. Although the 872 bp 3' flanking region of the cap5 promoter has been used in some embodiments of the present invention, it is envisioned that other sequences that are 3' to the cap5 promoter may be used to create a 3' flanking region. Additionally, it is envisioned that DNA sequences that are substantially similar to the 3' flanking region of the cap5 promoter may be used in various embodiments of the present invention. Therefore, the example should not be construed as limiting.

The DNA comprising SEQ ID NO:2 (250 by cap1 promoter) has been joined to the DNA comprising SEQ ID NO:3 (872 bp 3' flanking region of the cap5 promoter) by overlapping PCR according to the method of Higuchi. (1) The PCR primer Ppa8af7 (SEQ ID NO:11) is partially complementary to the sequence of PCR primer Ppa1r (SEQ ID NO:10) as shown in FIGS. 1 and 2A. More specifically, the 3' tail of SEQ ID NO:2 generated by PCR with primers Ppa1fNcoI (SEQ ID NO:13) and Ppa1r (SEQ ID NO:10) is identical to the 5' tail of SEQ ID NO:3 generated by PCR with primers Ppa8af7 (SEQ ID NO:11) and Ppa5ar1 (SEQ ID NO:8) as previously described. More specifically still, bases 218-250 of SEQ ID NO:2 are complementary to bases 1-33 of the complementary strand of SEQ ID NO:3. The double-stranded DNA comprising SEQ ID NO:2 and SEQ ID NO:3 were dissociated, annealed and elongated and then amplified by PCR using the PCR primers Ppa1fNcoI (SEQ ID NO:13) and Ppa5ar1 (SEQ ID NO:8) to generate a 1,089 by PCR product comprising the cap1 promoter joined to the 3' flanking region of the cap5 promoter. The 1,089 by PCR product is identified as SEQ ID NO:4. This 1,089 by PCR product was ligated into pGEM T-vector (Promega, Madison, Wis.) and verified by sequencing.

DNA comprising SEQ ID NO:4 as ligated into pGEM T-vector was digested with the restriction enzymes NcoI and BamHI and purified according to standard techniques. (2)

DNA comprising SEQ ID NO:1 was generated by PCR. The PCR product was ligated into pGEM T-vector (Promega, Madison, Wis.) and verified by sequencing. The vector with the SEQ ID NO:1 insert was digested with restriction enzymes EcoRI and NcoI and purified according to standard techniques. (2)

EcoRI and NcoI digested DNA comprising SEQ ID NO:1 and NcoI and BamHI digested DNA comprising SEQ ID NO:4 were ligated such that the resulting DNA of the ligation comprised a 5' flanking region of the cap5 promoter ligated to a cap1 promoter that is operably linked to a 3' flanking region of the cap5 promoter as shown in FIG. 2. This DNA sequence is the modified 5' control region and is 1,858 by in length as identified by SEQ ID NO:5. The modified 5' control region was verified by sequencing.

Figure 4:
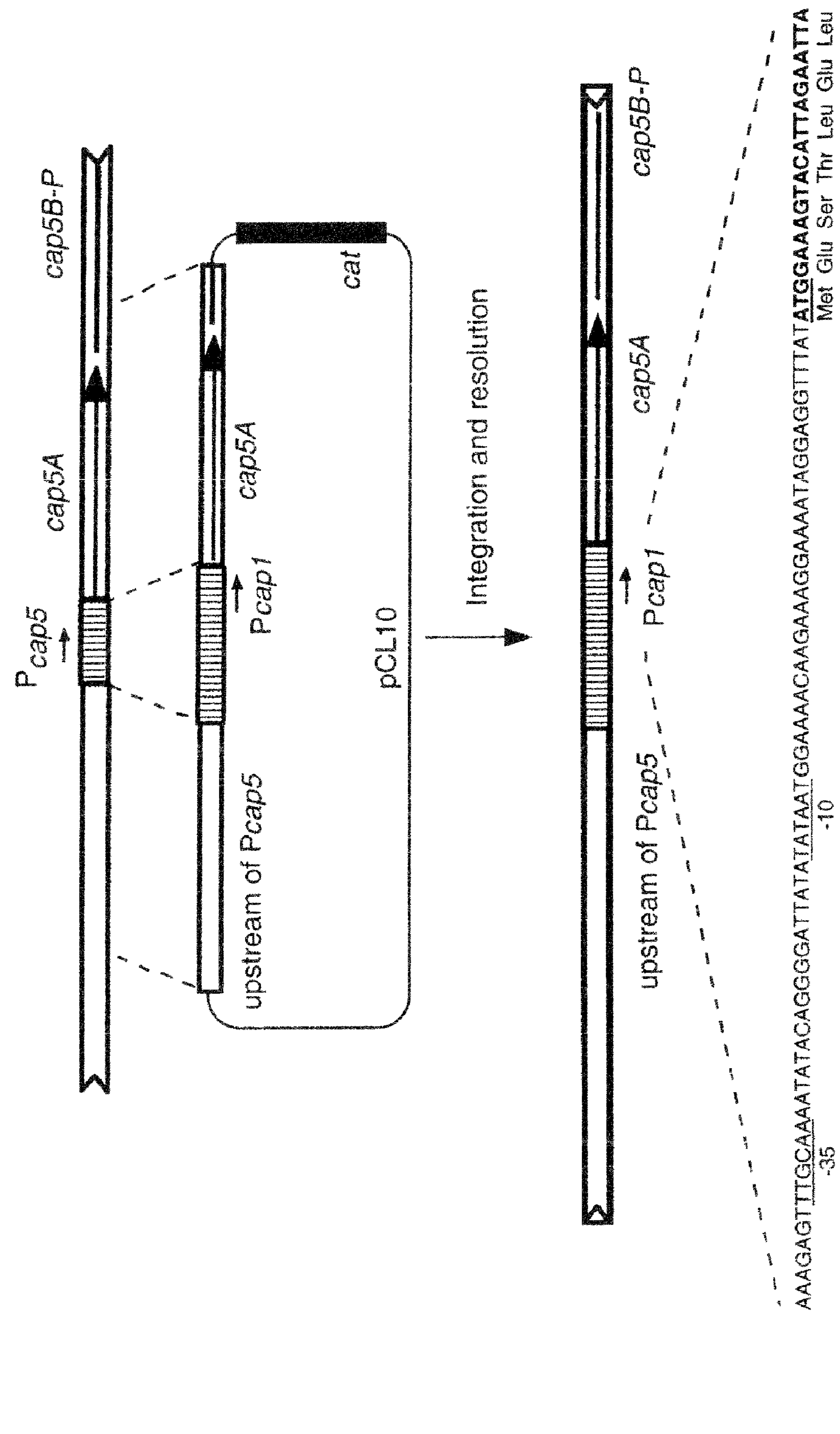
FIG. 4 illustrates the modified 5' control region ligated into the shuttle vector pCL10 in relation to the native cap5 operon of *Staphylococcus aureus* strain Reynolds. Additionally.

The shuttle vector pCL10 was digested with EcoRI and BamHI. The DNA comprising SEQ ID NO:5 that comprised DNA digested with EcoRI and BamHI restriction enzymes was purified and ligated into digested pCL10 as shown in FIG. 4. The resulting plasmid is a pCL10-modified 5' control region plasmid. pCL10 has been previously described. (3)

In various embodiments of the present invention, the pCL10-modified 5' control region plasmid may be introduced into a first host bacterial strain such as, for example, RN4220. The plasmid may be transferred via transduction from the first host bacterial strain to a second host bacterial strain such as, for example, *S. aureus* strain Reynolds.

In various embodiments of the present invention, electroporation may be used to introduce plasmids into *S. aureus*. Electroporation may be carried out by the following procedure:

1. Culture *S. aureus* strain RN4220 in sterile Trypticase Soy Broth ("TSB") overnight at 37° C. with agitation at approximately 225 revolutions per minute ("RPM"). Dilute the overnight culture 1:100 in TSB and incubate at 37° C. with agitation at approximately 225 RPM until the optical density at 660 nanometers ("$OD_{660}$") is in the range of approximately 0.3 to approximately 0.8 absorbance units. In various embodiments of the present invention, it may take approximately 2 hours and 10 minutes for the culture of RN4220 to reach an $OD_{660}$ of 0.32.
2. The culture may then be centrifuged at 10,000 RPM for 10 minutes to pellet the cells. The cell pellet may be resuspended in 0.8× volume of filter-sterilized 500 millimolar sucrose solution made from ultra-pure grade sucrose. The resuspended cells may be incubated on ice for approximately 30 minutes.
3. The resuspended cells may be centrifuged at 10,000 RPM for 10 minutes, the supernatant removed and the cells resuspended in 0.5× volume of filter-sterilized 500 millimolar sucrose solution made from ultra-pure grade sucrose. The resuspended cells may be incubated on ice for approximately 30 minutes.
4. The resuspended cells may be centrifuged at 10,000 RPM for 10 minutes, the supernatant removed and the cells resuspended in 0.01× volume of filter-sterilized 500 millimolar sucrose solution made from ultra-pure grade sucrose.
5. The resuspended competent cells may then be frozen in 125 μl aliquots in Eppendorf tubes on EtOH/dry-ice and subsequently stored at −70° C., or the competent cells may be used immediately for transformations.

6. Approximately 40 μl of the competent cells and 2 μl of plasmid DNA (approximately 0.5 μg/μl) may be added to a 0.2 cm electroporation cuvette. The mixture may be forced to the bottom by a quick shake.
7. The competent cells may be transformed by subjecting the electroporation cuvette containing the competent cells and the DNA to electroporation at 25 μF, 2.5 KV, and approximately 100Ω, approximately 200Ω, approximately 300Ω or approximately 400Ω.
8. Immediately after electroporation, approximately 250 μl TSB may be added to the cuvette. The cells may be withdrawn by a pipette. The cells may be introduced to agar plates comprising selective medium and incubated overnight at 37° C.

In various embodiments of the present invention, transduction of a recipient strain may be carried out with bacteriophage. The bacteriophage used in the transduction may be prepared as follows:

1. A host strain may be cultured overnight at 37° C. with agitation at approximately 225 RPM in appropriate selective medium. In various embodiments, the host strain may be RN4220 which has been transformed by electroporation with the pCL10-modified 5' control region plasmid. The overnight culture may be diluted 1:10 into 100 milliliters of TSB to make a new culture.
2. Incubate the new culture at 37° C. with agitation at approximately 225 RPM for approximately 1 hour 15 minutes to approximately 1 hour 30 minutes.
3. Four milliliters of 10 mg/ml $CaCl_2$ may be added to the new culture.
4. Bacteriophage may be added to the new culture at a Multiplicity of Infection ("MOI") of approximately 0.1. In various embodiments, the bacteriophage may be bacteriophage 52A.
5. The bacteriophage-infected new culture may be incubated at room temperature (approximately 25° C.) for approximately 30 minutes.
6. The bacteriophage-infected new culture may be agitated slowly at approximately 2 to approximately 3 hours at 30° C. The bacteriophage-infected new culture may be mixed and incubated overnight.
7. The cell debris may be pelleted by centrifugation and the supernatant purified by filter-sterilization. The filter-sterilized supernatant or lysate may contain bacteriophage comprising the pCL10-modified 5' control region plasmid.
8. The resulting filter-sterilized bacteriophage preparation may be tittered by serial dilution of the bacteriophage lysate in phage buffer. To each 0.1 milliliter of serially diluted bacteriophage lysate, add 0.2 milliliters sterile $CaCl_2$ (10 mg/ml), 0.2 milliliters of an appropriate bacterial strain, 4.5 ml soft agar (0.5% agar of Trypticase Soy Agar) and plate.
9. The plates may be incubated at 37° C. from approximately 6 hours to approximately 24 hours or alternatively until clear plaques are visible against a hazy lawn of bacteria. Bacteriophage titers may be obtained by counting the plaques present on plates and accounting for the appropriate dilution factor.
10. Phage buffer may be prepared as follows: Combine 6.47 grams of beta-glycerol phosphate, 0.12 grams of $MgSO_4.7H_2O$, 2.4 grams NaCl, 0.5 grams gelatin, and 477.5 milliliters of $H_2O$. Autoclave the solution. Add 22.5 milliliters of cool, sterile 10 mg/ml $CaCl_2$.

In various embodiments of the present invention, transduction of a recipient strain such as, for example, *S. aureus* strain Reynolds, may be carried out with bacteriophage such as, for example, bacteriophage 52A, according to the following procedure:

1. The recipient strain may be cultured in 3 milliliters of TSB overnight at 37° C. with agitation at approximately 225 RPM.
2. Approximately 1 milliliter of the overnight culture may be used to inoculate 100 milliliters of fresh TSB to make a new recipient culture.
3. The new recipient culture may be incubated at 37° C. with agitation at approximately 225 RPM until about $5\times10^7$ to about $1\times10^8$ colony forming units per milliliter ("cfu/ml") is obtained. The $OD_{660}$ of the culture should be approximately 0.1 within about 1 hour 15 minutes to about 1 hour 30 minutes.
4. The cultured cells may be pelleted by centrifugation at 10,000 RPM for approximately 5 minutes or approximately 10 minutes or such time as is necessary.
5. The cells may be washed with approximately 5 to 10 milliliters of TSB and pelleted by centrifugation.
6. The cells may be resuspended in 1 milliliter of TSB.
7. An aliquot of 0.1 milliliters of the resuspended cells may be removed for a total plate count and another 0.1 milliliter aliquot may be removed for plating to observe spontaneous mutants on selective agar.
8. To the remaining 0.8 milliliter, 0.1 milliliter of 10 mg/ml $CaCl_2$ may be added.
9. Bacteriophage may be added to the recipient cells to a multiplicity of infection of approximately 0.1 to approximately 1.0. For chromosomal markers, 0.8 ml phage lysate and 0.2 ml of 10 mg/ml $CaCl_2$ may be used.
10. The cells may be incubated at room temperature for approximately 10 minutes or such time as is necessary for adsorption of the phage to the cells.
11. In some instances it may be necessary to add 1 milliliter of cold 0.02 molar sodium citrate. This step is not required if bacteriophage 52A is utilized.
12. The cells may be incubated at 30° C. for 35 minutes without agitation, such as, for example, in a 30° C. water bath.
13. The cells may be diluted in 10 milliliters TSB, pelleted by centrifugation and resuspended in 10 milliliters TSB. The cells may be incubated at 37° C. for about 1 hour at approximately 225 RPM.
14. The cells may be pelleted by centrifugation and resuspended in about 1 milliliter of TSB. A portion of the resuspended cells such as, for example, 0.1 milliliters may be plated to a selective agar plate.
15. The selective agar plates may be incubated at 37° C. for approximately 24 hours to approximately 48 hours. Colonies, some of which may be transduced colonies, may form that are distinct from a background haze. In some instances, transductants may be visible in approximately 24 hours.

In various embodiments of the present invention, the pCL10-modified 5' control region plasmid is introduced into strain RN4220 bacteria by electroporation. In various embodiments of the present invention, the pCL10-modified 5' control region plasmid is introduced into *S. aureus* strain Reynolds via bacteriophage transduction. Furthermore, he 5' flanking region of the cap5 promoter and the 3' flanking region of the cap5 promoter which are part of the modified 5' control region are homologous to sequences of the *S. aureus* strain Reynolds genomic DNA. During replication of *S. aureus* strain Reynolds which has been transduced with the plasmid DNA comprising the modified 5' control region, the modified 5' control region may be integrated into the genomic DNA of *S. aureus* by homologous recombination. The homologous recombination event may occur such that the cap5 promoter sequence within the *S. aureus* genome is replaced by the cap1 promoter sequence encoded within the modified 5' control region of the plasmid. The resulting strain of *S. aureus* comprises a cap5 operon controlled by a constitutive promoter. Further, the resulting strain comprises a constitutive promoter operably linked to a cap5 operon. Further still, the resulting strain comprises a cap1 promoter operably linked to a cap5 operon. The DNA sequence of the constitutive promoter operably linked to the cap5 operon has been verified by sequencing. The resulting strain is CYL1892.

In various embodiments of the present invention, a strain of *Staphylococcus aureus* of the present invention comprises a DNA sequence comprising the cap1 promoter operably linked to the genes of the cap5 operon wherein the genes of the cap5 operon comprise the genes cap5A through cap5P as listed in SEQ ID NO:6. In various embodiments of the present invention, a strain of *Staphylococcus aureus* of the present invention comprises a DNA sequence comprising the cap1 promoter operably linked to the genes of the cap5 operon wherein the genes of the cap5 operon comprise the genes cap5A through cap5O as listed in SEQ ID NO:7.

The following examples are further illustrative of the present invention, but it is understood that the invention is not limited thereto.

Figure 5:
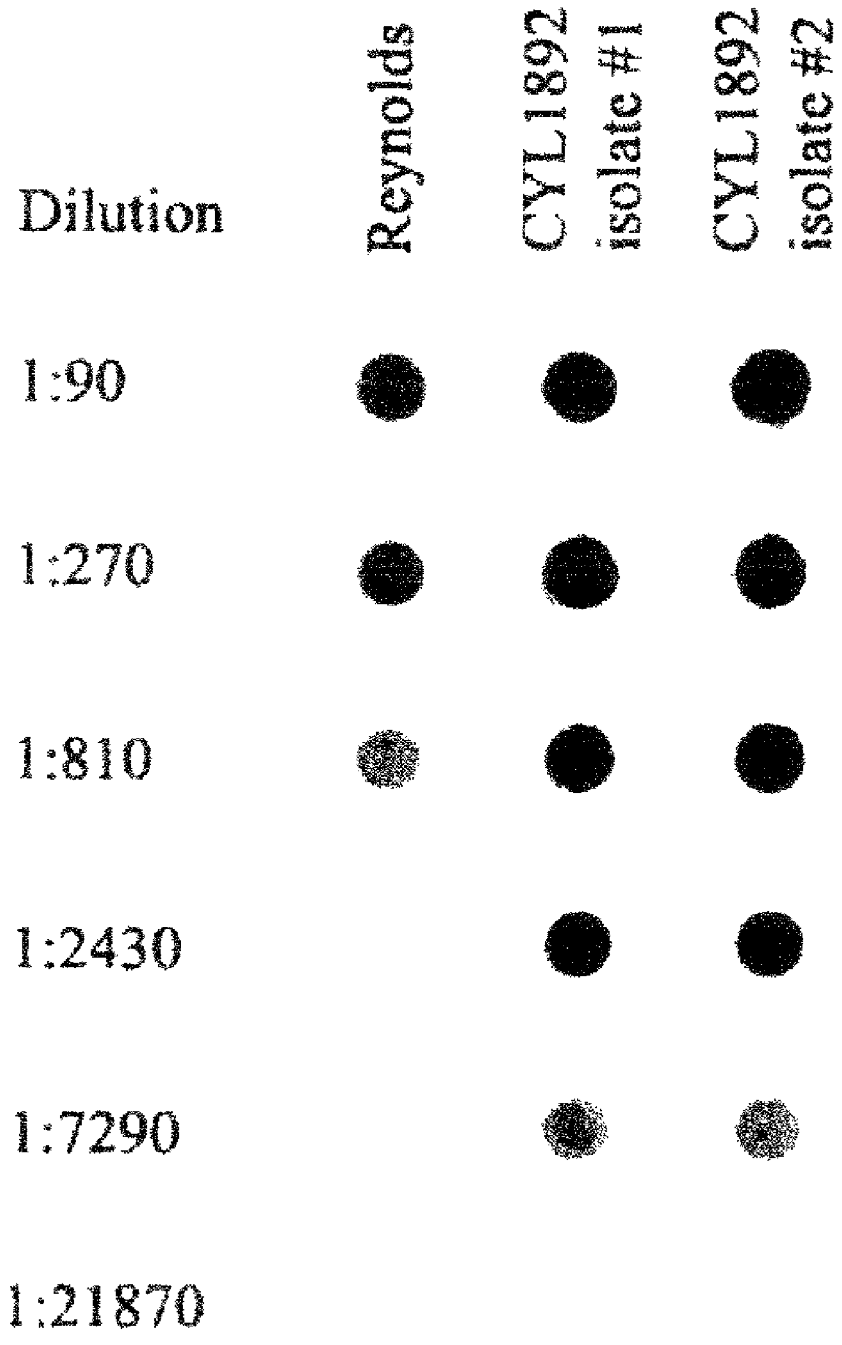
FIG. 5 illustrates differences in type 5 capsular polysaccharide production from a liquid culture of *Staphylococcus aureus* strain Reynolds and two independent liquid cultures of *Staphylococcus aureus* strain CYL1892 as detected by immuno-dot blotting.

FIG. 5 illustrates type 5 capsular polysaccharide production in one culture of *S. aureus* strain Reynolds and two independent cultures of *S. aureus* strain CYL1892. Cell-associated capsular polysaccharide may be dissociated as follows:

1. *S. aureus* strain Reynolds and *S. aureus* strain CYL1892 may be cultured overnight in TSB at 37° C. with agitation at approximately 225 RPM.
2. The $OD_{660}$ of 1:10 dilutions of overnight cultures of cultures of *S. aureus* strain Reynolds and *S. aureus* strain CYL1892 may be determined.
3. Cells from 1 milliliter of each culture may be pelleted by centrifugation and the cells from each sample may be resuspended in 10 μl of 1× Phosphate buffered saline ("PBS") per $OD_{660}$ unit.
4. One ml of Lysostaphin (10 mg/ml) may be added to the resuspended cells and the mixture incubated at 37° C. for approximately 15 minutes.
5. Subsequently, 0.4 μl of DNase I (75 ug/μl) may be added to the mixture and further incubated at 37° C. for approximately 15 minutes.
6. Cell debris may be pelleted by centrifugation. To the supernatant, 1 μl of Proteinase K (10 mg/ml) may be added and the mixture further incubated at 37° C. for approximately 30 minutes. Another 1 μl of Proteinase K (10 mg/ml) may be added to the previous mixture and said mixture further incubated at 37° C. for approximately 30 minutes.
7. The mixture may be heated at 75° C. for approximately 10 minutes and centrifuged to remove debris. The supernatant may contain capsular polysaccharide for further analysis.

Immuno-dot blotting may be performed according to the following procedure:

1. A vacuum dot-blot apparatus may be prepared by cleaning the apparatus including the manifold of the apparatus with distilled water.
2. A section of nitrocellulose paper may be soaked in 1× PBS for 10 minutes.
3. The wet nitrocellulose paper may be placed on the manifold and unnecessary air should be removed. The apparatus should be further assembled as necessary.
4. All sample chambers may be washed with 1× PBS by applying 1× PBS to each chamber and removing the 1× PBS by vacuum. The sample chambers should be refilled with 1× PBS.
5. Capsule samples may be serially diluted approximately two-fold to three-fold in approximately 30 μl to approximately 50 μl of 1× PBS.
6. Vacuum pressure should be used to remove the 1× PBS in the sample chambers. After removal, the vacuum pressure should be discontinued.
7. Serially diluted samples may be applied to the sample chambers. Gentle vacuum pressure should be applied. After all fluid in the sample chamber has been removed by vacuum, each sample chamber may be washed with 1 milliliter of 1× PBS by application of the 1× PBS to the sample chambers and removal by vacuum. Vacuum pressure may be applied for approximately 5 or more minutes to dry the nitrocellulose paper.
8. The nitrocellulose paper may be removed from the vacuum dot blot apparatus and placed into a container.
9. The nitrocellulose paper in the container may be incubated in approximately 10 milliliters of TS-skim milk at room temperature for approximately 1 hour with mild agitation. The container may be covered.
10. The nitrocellulose paper may be washed twice with approximately 15 milliliters of TS per wash.
11. The nitrocellulose paper may be incubated in 10 milliliters of TS-skim milk comprising anti-type 5 capsule primary rabbit antibody (kindly provided by Dr. Ali Fattom of NABI in Rockville, Md.) at room temperature for approximately 1 hour with mild agitation. The incubation may occur in a covered container.
12. The nitrocellulose paper may be washed three times with approximately 15 milliliters of TS per wash.
13. The nitrocellulose paper may be incubated in 10 milliliters of TS-skim milk comprising horseradish-peroxidase conjugated goat anti-rabbit at room temperature for approximately 1 hour with mild agitation. The incubation may occur in a covered container.
14. The nitrocellulose paper may be washed twice with approximately 15 milliliters of TS per wash. The nitrocellulose paper may be exposed to color development reagent.

10× PBS (pH 7.5) comprises the following: 0.06 grams of $KH_2PO_4$, 1.85 grams of $Na_2HPO_4$, 7.65 grams of NaCl and $H_2O$ to 100 milliliters. 10× TS comprises the following: 0.1M Tris-Cl (pH 7.5) and 1.5M NaCl. TS-skim milk comprises the following: 1× TS and 5% skim milk freshly prepared for each use and slightly warmed in a microwave oven.

Color developing reagent comprises the following: i) 12 mg HRP color developing reagent (BioRad) in 4 milliliters of Methanol; and ii) 0.012 milliliters of 30% $H_2O_2$ in 20 milliliters of TS. Parts i) and ii) of the color developing reagent should be mixed immediately prior to application.

Quantitation of type 5 capsular polysaccharide production illustrated in FIG. 5 was performed using a Kodak Molecular Image System. The results indicated that strain CYL1892 produced about 11.5 fold more type 5 capsular polysaccharide than strain Reynolds. In various embodiments of the present invention, a *Staphylococcus aureus* strain comprising a constitutive promoter operably linked to a cap5 operon may produce about 5 fold more type 5 capsular polysaccharide, about 9 fold more type 5 capsular polysaccharide, or about 11.5 fold more type 5 capsular polysaccharide than strain Reynolds.

Figure 6:
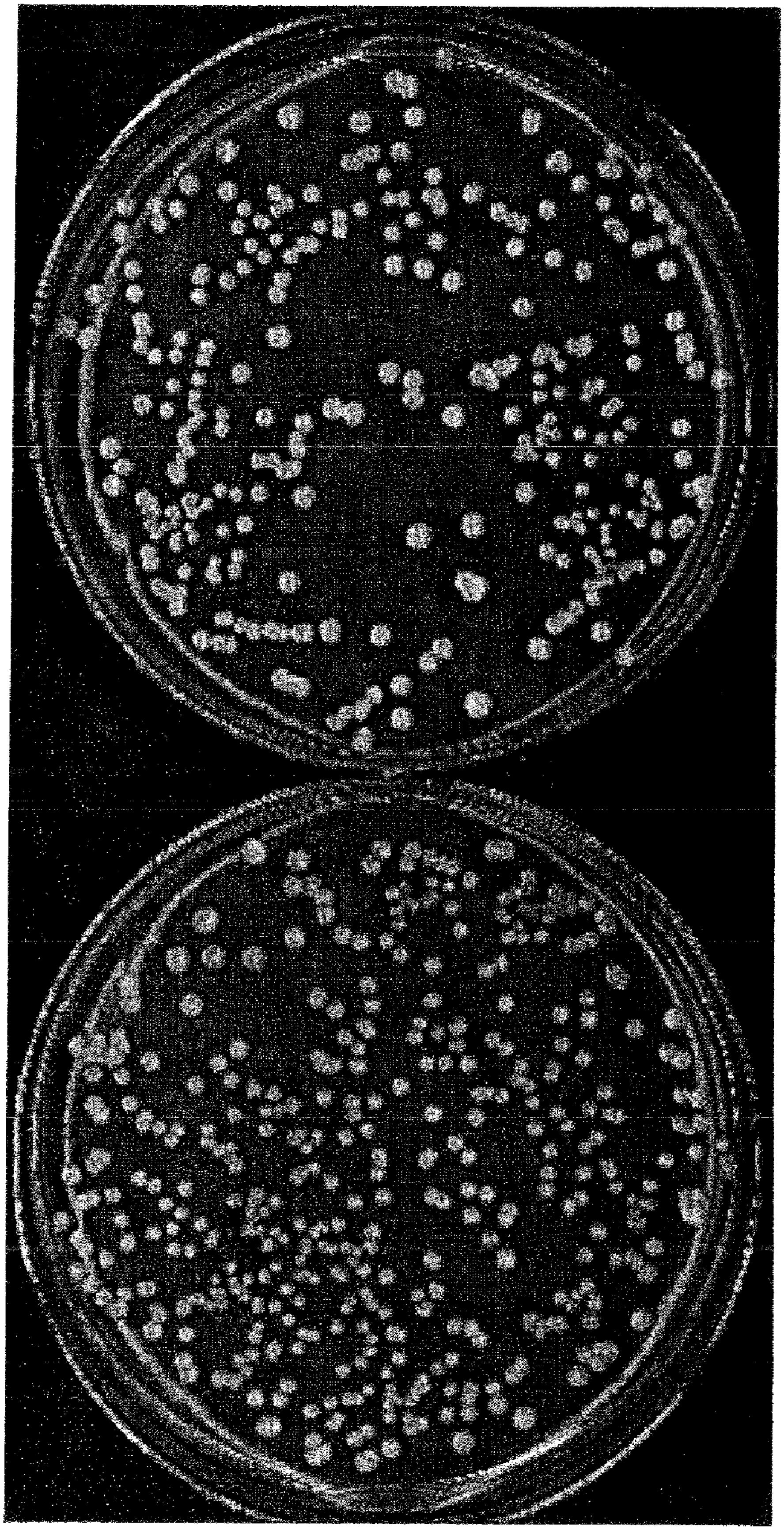
FIG. 6 illustrates differences in morphology between *Staphylococcus aureus* strain Reynolds (left) and *Staphylococcus aureus* strain CYL1892 (right).

The overproduction of type 5 capsular polysaccharide in CYL1892 is demonstrated on solid agar plates. FIG. 6 compares the gross morphology of *S. aureus* strain Reynolds (left) and *S. aureus* strain CYL1892 (right) after approximately 40 hours of growth at 30° C. on solid Trypticase Soy Agar plates. As shown in FIG. 6, CYL1892 has a larger colony size and more mucoid appearance on Trypticase Soy Agar plates than the strain Reynolds. Accepting that mucoid appearance is indicative of capsule production, these results indicate that the engineered strain CYL1892 constitutively produces more type 5 capsular polysaccharide than the wild-type strain.

In various embodiments of the present invention, PCR may be carried out using the Advantage HF-2 PCR kit from Stratagene according to the manufacturer's instructions. The PCR may comprise the following protocol:

1. 95° C. for 30 seconds;
2. 95° C. for 60 seconds;
3. 60° C. for 180 seconds;
4. Repeat parts 2 and 3 for 30 cycles; and
5. 60° C. for 300 seconds.

In various embodiments of the present invention, plasmid DNA may be purified with a plasmid purification kit (Qiagen, Inc., Chatsworth, Calif.). PCR products may be separated by agarose gel electrophoresis and purified by a PCR product purification kit (Qiagen, Inc., Chatsworth, Calif.). Bulk chromosomal DNA from *S. aureus* may be purified with a chromosomal DNA purification kit (Promega, Madison, Wis.). PCR amplification may be carried out with the Advantage cDNA PCR kit (Clontech, Palo Alto, Calif.) or the Advantage HF-2 PCR kit (Stratagene, La Jolla, Calif.). Unless otherwise described but without being limited thereto, standard DNA manipulations and other molecular biology techniques may be performed as described by Sambrook, et al. (2).

Genomic DNA from *S. aureus* strain Reynolds, a type 5 capsular polysaccharide producing strain containing the cap5 locus, was used as the template for the 5' flanking region of the cap5 promoter and the 3' flanking region of the cap5 promoter. Genomic DNA from *S. aureus* strain M, a type 1 capsular polysaccharide producing strain containing the cap1 locus, was used as the template for the cap1 promoter.

*S. aureus* RN4220 was used as the recipient in electroporations of the pCL10-modified 5' control region plasmid.

Bacteriophage 52A was used to transduce pCL10-modified 5' control region plasmid from RN4220 to *S. aureus* strain Reynolds.

*S. aureus* strain Reynolds, a type 5 capsular polysaccharide producing strain containing the cap5 locus, was used as the parent strain for constructing the type 5 capsular polysaccharide overproducing strain, CYL1892. *S. aureus* strain Reynolds was transduced with bacteriophage comprising the pCL10-modified 5' control region plasmid. *S. aureus* strain CYL1892 resulted from homologous recombination of the pCL10-modified 5' control region plasmid with *S. aureus* strain Reynolds genomic DNA.

*Escherichia coli* strain XL1-Blue was used as a host strain for plasmid constructions.

*S. aureus* strains were cultured in Trypticase soy medium (Difco Laboratories, Detroit, Mich.). *E. coli* strains were cultured in Luria-Bertani medium (Difco Laboratories). Where applicable, bacteria were cultured on agar plates containing the appropriate aforementioned media and 0.5% agar.

In various embodiments of the present invention, DNA sequences are listed as single-stranded DNA sequences. These sequences should not be construed to be limited to merely the single strand of DNA but should be construed to encompass a complementary strand where applicable.

All references cited in this specification are hereby incorporated by reference in their entirety. The discussion of the references herein is intended merely to summarize the assertions made by their authors and no admission is made that any reference constitutes prior art relevant to patentability. Applicant reserves the right to challenge the accuracy and pertinence of the cited references.

As various changes could be made in the above methods and compositions without departing from the scope of the invention, it is intended that all matter contained in the above description be interpreted as illustrative and not in a limiting sense. Unless explicitly stated to recite activities that have been done (i.e., using the past tense), illustrations and examples are not intended to be a representation that given embodiments of this invention have, or have not, been performed.

REFERENCES

1. Higuchi, R. 1989. Using PCR to engineer DNA, p. 61-70. In H. A. Erlich (ed.), PCR technology. Stockton Press, New York, N.Y.
2. Sambrook, J., E. F. Fritsch, and T. Maniatis. 1989. Molecular cloning: a laboratory manual, 2nd ed. Cold Spring Harbor Laboratory, Cold Spring Harbor, N.Y.
3. S. Sau, J. Sun and C. Y. Lee. 1997. Molecular characterization and transcriptional analysis of type 8 capsule genes in *Staphylococcus aureus*. J. Bacteriol. 179:1614-1621.

What is claimed is:

1. An isolated deoxyribonucleic acid sequence comprising SEQ ID NO: 7.

2. A strain of *Staphylococcus aureus* comprising the isolated deoxyribonucleic acid sequence of claim 1.

3. A strain of *Staphylococcus aureus* comprising an isolated DNA sequence comprising the cap1 promoter operably linked to the genes of the cap5 operon wherein the genes of the cap5 operon comprise the genes cap5A through cap5O as listed in SEQ ID NO: 7.

4. A strain of *Staphylococcus aureus* comprising an isolated DNA sequence, said DNA sequence comprising a constitutive promoter wherein said constitutive promoter is operably linked to a cap5 operon wherein said constitutive promoter is the cap1 promoter of *Staphylococcus aureus* strain M comprising SEQ ID NO: 2, and wherein the cap1 promoter and cap5 operon comprise the deoxyribonucleic acid sequence SEQ ID NO: 7.

* * * * *

UNITED STATES PATENT AND TRADEMARK OFFICE

CERTIFICATE OF CORRECTION

PATENT NO. : 8,097,446 B2
APPLICATION NO. : 12/398821
DATED : January 17, 2012
INVENTOR(S) : Chia Y. Lee et al.

It is certified that error appears in the above-identified patent and that said Letters Patent is hereby corrected as shown below:

On the title page, item (54) and col. 1, line 1, title
"STAPHYLOCOCUS" should read --STAPHYLOCOCCUS--

Signed and Sealed this
Thirteenth Day of March, 2012

David J. Kappos
*Director of the United States Patent and Trademark Office*

SEQUENCE LISTING

```
<160> NUMBER OF SEQ ID NOS: 13

<210> SEQ ID NO 1
<211> LENGTH: 778
<212> TYPE: DNA
<213> ORGANISM: Staphylococcus aureus

<400> SEQUENCE: 1

gaattcgagt ctacaagcga ttaaattgac gttcgaatat ttaaaatcat ctgttgaaaa      60

gggtgataaa gtttcaagag agaaaatgca taacgcatca actttggctg gtatggcatt     120

tgcaaatgca ttcttaggca ttgcacactc aattgcacat aaaattggtg gcgaatatgg     180
```

-continued

```
tattccgcat ggtagagcga atgcgatatt actaccgcat attatccgtt ataatgccaa    240

agacccgcaa aaacatgcat tattccctaa atatgagttc ttcagagcag atacagatta    300

tgcagatatt gccaaattct taggattaaa agggaatacg acagaagcac tcgtagaatc    360

attagctaaa gctgtctacg aattaggtca atcagtcgga attgaaatga atttgaaatc    420

acaaggtgtg tctgaagaag aattaaatga atcaattgat agaatggcag agctcgcatt    480

tgaagatcaa tgtacaactg ctaatcctaa agaagcacta atcagtgaaa tcaaagatat    540

cattcaaaca tcatatgatt ataagcaata atctatctga taataatcat ataactcacc    600

tgaaattaca aaagtaaaaa atgccacata aactttaagt cgataatcat tttacggtta    660

tcggctttta tttattgcca aatcttcaga gatacaaact agacaatcat ttttttaaat    720

aaagaaaata ttaagattga tactcatttc gcaaactatt actactttag agccatgg      778
```

```
<210> SEQ ID NO 2
<211> LENGTH: 250
<212> TYPE: DNA
<213> ORGANISM: Staphylococcus aureus

<400> SEQUENCE: 2

cggccatggc cacagtataa attatatcag tatgcttata taatttttga aatctttaaa     60

caaatgaagt aataattgag aaaagtgtag ttaaattatt tttcttgaaa ttatttgtta    120

catagcattt cgatgtaaaa ttcacttttt ataagtaaat ttaaaaagag tttgcaaaat    180

atacagggga ttatatataa tggaaaacaa gaaaggaaaa taggaggttt atatggaaag    240

tacattagaa                                                           250
```

```
<210> SEQ ID NO 3
<211> LENGTH: 872
<212> TYPE: DNA
<213> ORGANISM: Staphylococcus aureus

<400> SEQUENCE: 3

aaataggagg tttatatgga aagtacatta gaattaacaa aaattaaaga agtattacaa     60

aaaaacttga agattttaat tattttaccg ctattatttt taattattag cgctattgtt    120

acatttttcg tcttatcacc taaatatcaa gctaatactc aaatcttagt gaatcaaact    180

aagggtgaca atcctcagtt tatggcacaa gaggttcaaa gtaatattca acttgtaaat    240

acgtataaag aaattgttaa aagtcctaga attttagatg aggtgtcaaa ggacttaaat    300

gataagtatt caccatctaa attgtcgagt atgttgacaa ttacaaacca agaaaatacg    360

caacttatca acatccaagt taaaagtggt cataaacaag attcggaaaa aattgcgaat    420

agcttcgcta aagttacaag taaacaaatt ccgaagatta tgagtgtgga taacgtatca    480

attttatcta aagcagacgg tacagcagtt aaagtcgcac caaaaactgt agtgaatcta    540

atcggtgcat tctttttagg attagttgtc gcgcttatat atatcttctt caaagtaatt    600

ttcgataagc gaattaaaga tgaagaagat gtagagaaag aattaggatt gcctgtattg    660

ggttcaattc aaaaatttaa ttaaggatgg ttgctactta tgtcaaaaaa ggaaaatacg    720

acaacaacac tatttgtata tgaaaaacca aaatcaacaa ttagtgaaaa gtttcgaggt    780

atacgttcaa acatcatgtt ttcaaaagca aatggtgaag taaagcgctt attggttact    840

tctgaaaagc ctggtgcagg taaaagggat cc                                  872
```

```
<210> SEQ ID NO 4
<211> LENGTH: 1089
<212> TYPE: DNA
```

-continued

<213> ORGANISM: Staphylococcus aureus

<400> SEQUENCE: 4
cggccatggc cacagtataa attatatcag tatgcttata taatttttga aatctttaaa 60
caaatgaagt aataattgag aaaagtgtag ttaaattatt tttcttgaaa ttatttgtta 120
catagcattt cgatgtaaaa ttcacttttt ataagtaaat ttaaaaagag tttgcaaaat 180
atacagggga ttatatataa tggaaaacaa gaaaggaaaa taggaggttt atatggaaag 240
tacattagaa ttaacaaaaa ttaaagaagt attacaaaaa aacttgaaga ttttaattat 300
tttaccgcta ttatttttaa ttattagcgc tattgttaca tttttcgtct tatcacctaa 360
atatcaagct aatactcaaa tcttagtgaa tcaaactaag ggtgacaatc ctcagtttat 420
ggcacaagag gttcaaagta atattcaact tgtaaatacg tataaagaaa ttgttaaaag 480
tcctagaatt ttagatgagg tgtcaaagga cttaaatgat aagtattcac catctaaatt 540
gtcgagtatg ttgacaatta caaaccaaga aaatacgcaa cttatcaaca tccaagttaa 600
aagtggtcat aaacaagatt cggaaaaaat tgcgaatagc ttcgctaaag ttacaagtaa 660
acaaattccg aagattatga gtgtggataa cgtatcaatt ttatctaaag cagacggtac 720
agcagttaaa gtcgcaccaa aaactgtagt gaatctaatc ggtgcattct ttttaggatt 780
agttgtcgcg cttatatata tcttcttcaa agtaattttc gataagcgaa ttaaagatga 840
agaagatgta gagaaagaat taggattgcc tgtattgggt tcaattcaaa aatttaatta 900
aggatggttg ctacttatgt caaaaaagga aaatacgaca acaacactat ttgtatatga 960
aaaaccaaaa tcaacaatta gtgaaaagtt tcgaggtata cgttcaaaca tcatgttttc 1020
aaaagcaaat ggtgaagtaa agcgcttatt ggttacttct gaaaagcctg gtgcaggtaa 1080
aagggatcc 1089

<210> SEQ ID NO 5
<211> LENGTH: 1858
<212> TYPE: DNA
<213> ORGANISM: Staphylococcus aureus

<400> SEQUENCE: 5
gaattcgagt ctacaagcga ttaaattgac gttcgaatat ttaaaatcat ctgttgaaaa 60
gggtgataaa gtttcaagag agaaaatgca taacgcatca actttggctg gtatggcatt 120
tgcaaatgca ttcttaggca ttgcacactc aattgcacat aaaattggtg gcgaatatgg 180
tattccgcat ggtagagcga atgcgatatt actaccgcat attatccgtt ataatgccaa 240
agacccgcaa aaacatgcat tattccctaa atatgagttc ttcagagcag atacagatta 300
tgcagatatt gccaaattct taggattaaa agggaatacg acagaagcac tcgtagaatc 360
attagctaaa gctgtctacg aattaggtca atcagtcgga attgaaatga atttgaaatc 420
acaaggtgtg tctgaagaag aattaaatga atcaattgat agaatggcag agctcgcatt 480
tgaagatcaa tgtacaactg ctaatcctaa agaagcacta atcagtgaaa tcaaagatat 540
cattcaaaca tcatatgatt ataagcaata atctatctga taataatcat ataactcacc 600
tgaaattaca aaagtaaaaa atgccacata aactttaagt cgataatcat tttacggtta 660
tcggctttta tttattgcca aatcttcaga gatacaaact agacaatcat ttttttaaat 720
aaagaaaata ttaagattga tactcatttc gcaaactatt actactttag agccatggcc 780
acagtataaa ttatatcagt atgcttatat aatttttgaa atctttaaac aaatgaagta 840
ataattgaga aaagtgtagt taaattattt ttcttgaaat tatttgttac atagcatttc 900

-continued

```
gatgtaaaat tcacttttta taagtaaatt taaaaagagt ttgcaaaata tacaggggat    960
tatatataat ggaaaacaag aaaggaaaat aggaggttta tatggaaagt acattagaat   1020
taacaaaaat taaagaagta ttacaaaaaa acttgaagat tttaattatt ttaccgctat   1080
tatttttaat tattagcgct attgttacat ttttcgtctt atcacctaaa tatcaagcta   1140
atactcaaat cttagtgaat caaactaagg gtgacaatcc tcagtttatg gcacaagagg   1200
ttcaaagtaa tattcaactt gtaaatacgt ataaagaaat tgttaaaagt cctagaattt   1260
tagatgaggt gtcaaaggac ttaaatgata agtattcacc atctaaattg tcgagtatgt   1320
tgacaattac aaaccaagaa aatacgcaac ttatcaacat ccaagttaaa agtggtcata   1380
aacaagattc ggaaaaaatt gcgaatagct tcgctaaagt tacaagtaaa caaattccga   1440
agattatgag tgtggataac gtatcaattt tatctaaagc agacggtaca gcagttaaag   1500
tcgcaccaaa aactgtagtg aatctaatcg gtgcattctt tttaggatta gttgtcgcgc   1560
ttatatatat cttcttcaaa gtaattttcg ataagcgaat taaagatgaa gaagatgtag   1620
agaaagaatt aggattgcct gtattgggtt caattcaaaa atttaattaa ggatggttgc   1680
tacttatgtc aaaaaaggaa aatacgacaa caacactatt tgtatatgaa aaaccaaaat   1740
caacaattag tgaaaagttt cgaggtatac gttcaaacat catgttttca aaagcaaatg   1800
gtgaagtaaa gcgcttattg gttacttctg aaaagcctgg tgcaggtaaa agggatcc     1858
```

<210> SEQ ID NO 6
<211> LENGTH: 17566
<212> TYPE: DNA
<213> ORGANISM: Staphylococcus aureus

<400> SEQUENCE: 6

```
gagtctacaa gcgattaaat tgacgttcga atatttaaaa tcatctgttg aaaagggtga     60
taaagtttca agagagaaaa tgcataacgc atcaactttg gctggtatgg catttgcaaa    120
tgcattctta ggcattgcac actcaattgc acataaaatt ggtggcgaat atggtattcc    180
gcatggtaga gcgaatgcga tattactacc gcatattatc cgttataatg ccaaagaccc    240
gcaaaaacat gcattattcc ctaaatatga gttcttcaga gcagatacag attatgcaga    300
tattgccaaa ttcttaggat taaaagggaa tacgacagaa gcactcgtag aatcattagc    360
taaagctgtc tacgaattag gtcaatcagt cggaattgaa atgaatttga aatcacaagg    420
tgtgtctgaa gaagaattaa atgaatcaat tgatagaatg gcagagctcg catttgaaga    480
tcaatgtaca actgctaatc ctaaagaagc actaatcagt gaaatcaaag atatcattca    540
aacatcatat gattataagc aataatctat ctgataataa tcatataact cacctgaaat    600
tacaaaagta aaaaatgcca cataaacttt aagtcgataa tcattttacg gttatcggct    660
tttatttatt gccaaatctt cagagataca aactagacaa tcattttttt aaataaagaa    720
aatattaaga ttgatactca tttcgcaaac tattactact ttagagccat ggccacagta    780
taaattatat cagtatgctt atataatttt tgaaatcttt aaacaaatga agtaataatt    840
gagaaaagtg tagttaaatt atttttcttg aaattatttg ttacatagca tttcgatgta    900
aaattcactt tttataagta aatttaaaaa gagtttgcaa aatatacagg ggattatata    960
taatggaaaa caagaaagga aaataggagg tttatatgga aagtacatta gaattaacaa   1020
aaattaaaga agtattacaa aaaaacttga agattttaat tattttaccg ctattatttt   1080
taattattag cgctattgtt acatttttcg tcttatcacc taaatatcaa gctaatactc   1140
aaatcttagt gaatcaaact aagggtgaca atcctcagtt tatggcacaa gaggttcaaa   1200
```

-continued

```
gtaatattca acttgtaaat acgtataaag aaattgttaa aagtcctaga attttagatg   1260
aggtgtcaaa ggacttaaat gataagtatt caccatctaa attgtcgagt atgttgacaa   1320
ttacaaacca agaaaatacg caacttatca acatccaagt taaaagtggt cataaacaag   1380
attcggaaaa aattgcgaat agcttcgcta aagttacaag taaacaaatt ccgaagatta   1440
tgagtgtgga taacgtatca attttatcta aagcagacgg tacagcagtt aaagtcgcac   1500
caaaaactgt agtgaatcta atcggtgcat tctttttagg attagttgtc gcgcttatat   1560
atatcttctt caaagtaatt ttcgataagc gaattaaaga tgaagaagat gtagagaaag   1620
aattaggatt gcctgtattg ggttcaattc aaaaatttaa ttaaggatgg ttgctactta   1680
tgtcaaaaaa ggaaaatacg acaacaacac tatttgtata tgaaaaacca aaatcaacaa   1740
ttagtgaaaa gtttcgaggt atacgttcaa acatcatgtt ttcaaaagca aatggtgaag   1800
taaagcgctt attggttact tctgaaaagc ctggtgcagg taaaagtaca gttgtatcga   1860
atgtagcgat tacttatgca caagcaggct ataagacatt agttattgat ggcgatatgc   1920
gtaagccaac acaaaactat atttttaatg agcaaaataa taatggacta tcaagcttaa   1980
tcattggtcg aacgactatg tcagaagcaa ttacgtcgac agaaattgaa aatttagatt   2040
tgctaacagc tggccctgta cctccaaatc catctgagtt aattgggtct gaaaggttca   2100
aagaattagt tgatctgttt aataaacgtt acgacattat tattgtcgat acaccgccag   2160
ttaatactgt gactgatgca caactatatg cgcgtgctat taaagatagt ctgttagtaa   2220
ttgatagtga aaaaaatgat aaaaatgaag ttaaaaaagc aaaagcactt atggaaaaag   2280
caggcagtaa cattctaggt gtcattttga acaagacaaa ggtcgataaa tcttctagtt   2340
attatcacta ttatggagat gaataagtat gattgatatt cataaccata tattgcctaa   2400
tatcgatgac ggtccgacaa atgaaacaga gatgatggat cttttaaaac aagcgacaac   2460
acaaggtgtt acagaaatca ttgtaacatc acatcactta catcctcgat ataccacacc   2520
tatagaaaaa gtgaaatcat gtttaaacca tattgaaagc ttagaggaag tacaagcact   2580
aaatctaaag ttttattatg gtcaggaaat aagaattacc gatcaaatcc ttaatgatat   2640
tgatcgaaaa gttattaccg gtattaatga ttcacgctat ttactaatag aatttccatc   2700
aaatgaagtt ccacactata ctgatcaatt atttttcgaa ttacagagta aaggctttgt   2760
accgattatt gcacatccag agcgaaataa agcaataagt caaaaccttg acatactata   2820
cgatttaatt aacaaaggtg ctttaagtca agtgacaacg gcgtcattag cgggtatttc   2880
cggtaaaaaa attagaaaat tagcaattca aatgattgaa aacaatctga cacatttcat   2940
cggttcagat gcgcataaca cagaaatcag accgttctta atgaaagact tatttaatga   3000
taagaaatta cgtgattatt atgaagatat gaacggattt attagtaatg cgaagttagt   3060
tgttgatgat aaaaaaattc ctaaacgaat gccacaacaa gattataaac agaaaagatg   3120
gtttgggtta taaacagcaa atgaggggtt ttatggcaca tttatctgtg aaattgcggc   3180
ttttaatact agcattaatc gattcactga tagtgacatt ttcagtattc gtaagttatt   3240
acattttaga accgtatttc aaaacatatt ctgtcaaatt attaatattg gcagctatat   3300
cactattcat atcgcatcat atttcagcat ttattttttaa tatgtatcat cgagcgtggg   3360
aatatgccag tgtgagtgaa ttgattttaa ttgttaaagc tgtgacgaca tctatcgtta   3420
ttacgatggt ggtcgtgaca attgttacag gcaatagacc gtttttttaga ttgtatttaa   3480
ttacttggat gatgcacttg attttaatag gtggctcaag gttattttgg cgtatttatc   3540
ggaaatacct tggaggtaag tcatttaata agaagccaac tttagttgtt ggtgctggtc   3600
```

-continued

```
aagcaggttc aatgctgatt agacaaatgt tgaaaagtga cgaaatgaaa cttgaaccgg   3660
tattagcagt cgatgatgac gaacataaac gcaatatcac aattactgag ggtgtaaaag   3720
tccaaggtaa aattgcggat attccagaac tagtgaggaa atataagatt aaaaaaatca   3780
tcattgcaat tccaactatt ggtcaagagc gtttgaaaga aattaataat atttgccata   3840
tggatggcgt tgagttattg aaaatgccaa atatagaaga cgtcatgtct ggtgagttag   3900
aagtgaatca actgaaaaaa gttgaagtag aagatttact aggcagagat cctgttgaat   3960
tagatatgga tatgatatca aatgaattga cgaataaaac tattttagtt acgggtgcag   4020
gtggttcaat aggatcagaa atttgtagac aagtttgtaa tttctatcca gaacgtatta   4080
ttctacttgg ccatggtgaa aacagtattt atttaatcaa tcgtgaattg cgaaatcgct   4140
tcggaaaaaa tgttgatatc gttcctatta tagcggatgt gcaaaataga gcgcgtatgt   4200
ttgaaattat ggaaacgtat aaaccatacg cagtttatca tgcagcagca cacaagcacg   4260
tgccgttaat ggaagacaac cctgaagaag cagtacataa taatatttta ggtacgaaaa   4320
atactgctga agctgctaaa aatgcagagg taaagaaatt cgttatgatt tctacggata   4380
aagccgttaa tccgcctaat gtcatgggag cttcaaagcg aattgcagaa atgattattc   4440
aaagtttaaa tgatgaaacg catcgaacaa attttgttgc agtgagattt ggtaatgtac   4500
ttggatcgag aggatctgtg attccacttt tcaaaagtca aattgaagaa ggtgggccag   4560
ttactgtgac acatcctgaa atgacacgtt actttatgac aattcctgaa gcttctagac   4620
tagttttgca ggcaggggca ttagcagaag gtggcgaagt atttgtgcta gatatgggag   4680
aaccagtgaa aattgtagat ttggcacgta atttaattaa gctaagtggt aaaaaagaag   4740
acgacatacg cattacttat acagggatta gacccggcga aaaaatgttt gaagagctta   4800
tgaataaaga tgaggttcat cctgaacaag tatttgaaaa aatttatcgt ggcaaagtac   4860
aacatatgaa atgtaatgaa gttgaagcga ttattcaaga catcgtcaat gactttagta   4920
aagaaaaaat tattaactat gccaatggca aaaagggaga taattatgtt cgatgacaaa   4980
attttattaa ttactggggg cacaggatca ttcggtaatg ctgttatgaa acggttttta   5040
gattctaata ttaaagaaat tcgtattttt tcacgcgatg agaaaaaaca agatgacatt   5100
cgaaaaaaat ataataattc aaaattaaag ttctacattg gtgatgtgcg tgatagtcaa   5160
agtgtagaaa cagcaatgcg agatgttgat tacgtattcc atgcagcagc tttaaaacaa   5220
gtgccgtcat gtgaattctt tccagttgag gcagtgaaga caaatattat tggtacagaa   5280
aatgtcttac aaagtgctat tcatcaaaat gttaaaaaag tcatatgttt atctacagat   5340
aaggcagcgt atcctattaa tgctatgggt atttcaaaag caatgatgga aaaagtattc   5400
gtagccaaat caagaaatat tcgtagtgaa caaacgctta tttgtggtac aagatacggt   5460
aatgtgatgg cttcaagagg atcagtaata cctttgttta tcgacaaaat caaagctgga   5520
gaacctttaa cgattacaga tcctgatatg acaagatttt taatgagctt agaagatgcg   5580
gtagaactag ttgttcatgc atttaagcat gcagagacag gagatattat ggttcaaaaa   5640
gcaccaagct caacggtagg ggatcttgcg accgcattat tagaattgtt tgaagctgat   5700
aatgcaattg aaatcattgg tacgcgacat ggagagaaaa aagcagaaac attgttgacg   5760
agagaagaat acgcacaatg tgaagatatg ggtgattatt ttagagtgcc ggcagactcc   5820
agagatttaa attatagtaa ttatgttgaa accggtaacg aaaagattac gcaatcttat   5880
gaatataact ccgataatac acatatttta acggtggaag agataaaaga aaaactttta   5940
acactagaat atgttagaaa cgaattgaat gattataaag cttcaatgag ataggagaga   6000
```

-continued

```
ttgacgttga atattgtaat tacaggagca aaaggttttg taggaaaaaa cttgaaagca   6060
gatttaacat caacgacaga tcatcatatt ttcgaagtac atcgacaaac taaagaggaa   6120
gaattagagt cagcattgtt gaaagcagac tttatcgtgc atttagcggg tgttaatcga   6180
cctgaacatg acaaagaatt cagcttagga aacgtgagtt atttagatca tgtacttgat   6240
atattaacta gaaatacgaa aaagccagcg atattattat cgtcttcaat acaagcaaca   6300
caagataatc cttatggtga gagtaagttg caaggggaac agctattaag agagtatgcc   6360
gaagagtatg gcaatacggt ttatatttat cgctggccaa atttattcgg caagtggtgt   6420
aagccgaatt ataactcagt gatagcaaca ttttgttaca aaattgcacg taacgaagag   6480
attcaagtta atgatcggaa tgttgaacta acgctaaact acgtggatga tatcgtcgct   6540
gaaataaagc gtgctattga aggaactcca acgattgaaa atggtgtacc tacagtacca   6600
aacgtattta aagtgacatt gggagaaatt gtagatttat tatacaagtt caaacagtca   6660
cgtctcgatc gaacattgcc gaaattagat aacttgtttg aaaaagattt gtatagtacg   6720
tatttaagct atctacctag tacagacttt agttatccct tacttatgaa tgtggatgat   6780
aggggttctt ttacagaatt tataaaaaca ccggatcgtg gtcaagtttc tgtaaatatt   6840
tctaaaccag gtattactaa aggtaatcac tggcaccata ctaaaaacga aaaatttcta   6900
gtcgtatcag gtaaaggggt aattcgtttt agacatgtta atgatgatga aatcattgaa   6960
tattacgttt ctggcgataa attagaagtt gtagacatac cagtaggata cacacataat   7020
attgaaaatt taggcgacac agatatggta actattatgt gggtgaatga aatgtttgat   7080
ccaaatcagc cagatacgta tttcttggag gtatagcgca tggaaaaact gaaattaatg   7140
acaatagttg gtacaaggcc tgaaatcatt cgtttatcat caacgattaa agcatgtgat   7200
caatatttta atcagatatt agtacacact ggtcaaaatt atgattatac attgaatcaa   7260
attttctttg atgatttgga attaagacaa ccggaccact acttagaggc agttggaagt   7320
aaccttggag aaacgatggg gaatattatt gcgaagacat atgacgtttt attacgcgaa   7380
caaccagatg cacttttaat tcttggtgat acaaatagtt gtttagcagc agtatctgct   7440
aaacgattaa agattcctgt gttccacatg gaagcgggta atagatgctt tgatcagaat   7500
gtacctgaag aaatcaatcg taaaattgtt gaccatgtca gtgatgtgaa tctaccttat   7560
acagaacata gcagacggta tttattagat gaaggcttca ataaagcgaa tatctttgtg   7620
acaggatcac cgatgacaga agtgatagaa gcgcatcgag ataaaattaa tcacagtgac   7680
gttttaaata aactaggatt agaaccgcaa caatacattt tagtatctgc gcatagagaa   7740
gagaatatcg ataatgaaaa gaattttaaa tcattaatga atgcgataaa tgatattgcc   7800
aaaaagtata aaatgcctgt gatttattca acgcatccaa gaagttggaa gaaaattgaa   7860
gaaagtaaat ttgaatttga tccattagtt aaacagttaa agccatttgg tttctttgat   7920
tataatgcat tgcaaaaaga tgcatttgtt gtgctatcag atagtggaac attgtcagaa   7980
gagtcgtcta ttttgaagtt ccctggtgtc cttattcgaa cttccacaga aagaccggaa   8040
gtactagata aaggtacggt tattgtaggt ggtattacct ataacaatct aatccaatcc   8100
gttgaactag caagagagat gcaaaacaat aacgaaccga tgattgatgc tattgattat   8160
aaagacacta acgtttcgac aaaggtagtt aaaattattc aaagctataa agatattatc   8220
aatcgaaata cttggaggaa atgacgatga ggatagcgat tgaaaagata attggtttgc   8280
tgaaaaacca gtcctctaaa gaatcgaatg ttaagattca tcgcttggcg tatattacaa   8340
actcaaaatt tgatggcaat aactatatag atagatggtg taaaatcagg aattctcaca   8400
```

-continued

```
ttggtgaata cagttatatt ggatttggta gtgattttaa taatgtagaa gtaggaagat   8460
attgttcgat atcttcggat gtaaaaattg ggttaggaaa acatcctaca cacttttttta   8520
gctcatcacc gattttttat tctaataata atccatttaa cataaagcaa aagtttatag   8580
actttaatga ccaaccaagc cgtacaacaa ttaaaaatga tgtgtggatt ggtgcaaatg   8640
taattattat ggatggatta acaataaata ctggtgcagt catagcagcc ggctcagttg   8700
ttactaaaaa tgtaggagca tatgaggttg ttggtggggt tcctgcaaaa gtgattaaga   8760
agcgatttga caataaaaca attgaaaaac ttttggaaag caagtggtgg gagaaaacgc   8820
ctgacaaact aaaaggattt tcggttgaat atttaaataa aaaggatact taatgatatg   8880
agaattttaa atattgtatc gagtaatatt gttcaagacc caagggtact taaacaaata   8940
gaaacaatta aaggcgttac gaatgattat aaaattgttg gaatgaataa ttcacaagct   9000
actaataggc gattggaaaa tttagattgt aattatcgtt tgttaggtag caaggtagat   9060
cccaaaaata ttctttctaa attaattaag cgtataagat ttgcaacagg tgttatccga   9120
gaaattaaag cttttaaacc tgacgtgatt catgcaaatg atttcgacgt attattaatg   9180
gtctatttaa gcaattataa aaaagctaat attgtttatg atgcgcatga aatatatgcg   9240
aaaaatgcct ttattaataa agttccactt atttcaaagt ttgtagaaag tatagaaaaa   9300
cacatagtaa aacatcgtgt taatgccttc gtaacagtaa gtcatgcagc aaaagaatat   9360
tatcaatcta aaggatataa gaaggaagcg aatgttatta cgaatgcacc tattttaaat   9420
gatagcagag aatttaaaga aatcgaaaac tttaaagaaa tcgtatatca aggtcaaatt   9480
gtaatggaca gaggatatga agagtttatt attgcttcat cagcttttaa acaaaatgct   9540
ccttcattca taattcgagg gtttggtccg catgaagaag tgataaaaga actgattagt   9600
tataactcgg aaaatattag gttggataaa ccagttgaag taaaagaatt ggttgataag   9660
ttagcagaaa gtaatgttgg tgttatcttg acgaaacctg tatctattaa ttttgaatat   9720
acagtatcta ataaaatttt tgaatgtata catgctggtt taccagtaat tttatctcct   9780
gtcaaagagc atatttatct caatgaaaaa tataaatttg gcattgtttt aaaggaagtt   9840
acgccgttag aaattgaaaa ggcggttaga aaattaagag ataatcacga tttgtttaat   9900
catttacgtc aaaatgcaat taaggcgtct aaaattttga attggcaaat agaaagtgaa   9960
cgattagtag aattatataa attttaaaga gaggtaaact atgaaatttt ttgtactttg  10020
tgcaattatc agcatgaaca tatttatagt aatctctaca tttactaaag aagtattagg  10080
gttccctata gagccggtgt attactcaac catggttggt atagcattaa ttactacggt  10140
gtttgctatt tataagataa ttgtcacgca agaaattccg cgagggttaa tattattaat  10200
tgctatatgt ttgctttatc tagcttttta ttatttttca ccagataagg aagagaaact  10260
agctaaaaat aatattctat tctttttaac atgggcagtt ccagcggcaa ttagtggtat  10320
ttatattaaa tatataaaca aggctacggt agaaagattt tttaaattag tatttttcat  10380
attttctatt tcatttattt ttgtaatttt aataccaaaa cttacaggtg agatacctag  10440
ctatatcaat tttggactta tgaactatca aaacgcttcg tacctttcag catttactgc  10500
cggattaggc atttatttca ttatgaaagg ttcagtgaaa cataagtgga tatatgttct  10560
atttacaata attgatatcc ctattgtgtt tataccagga gggcgtggag gtgctatttt  10620
attaattctt tacggcttat ttgcatttat acttattacg tttaaaagag gaatacctat  10680
tgcagtaaaa agcattatgt atatttttgc attaagcata tctagtgtat tgatttactt  10740
tcttttttaca aaaggttcga atactagaac attttcatat ctacaaggtg gaacacttaa  10800
```

-continued

```
tttagaaggt acttctggaa gaggaccgat ttatgaaaaa ggtatttact ttattcaaca  10860
aagtccgtta ttaggctatg ggccatttaa ctattataaa ctaatcggaa atataccaca  10920
taacatcatt attgagttga ttctatcatt tggcttatta gggtttttta tcataatgat  10980
ttgcattttg ctactagttt ataaaatgat taggaactat gatccaaaca ctatagattt  11040
actcgttatg tttatagcaa tctatccaat cacattatta atgtttagtt caaattattt  11100
agttgtaagt gaattttggt ttgtgttgtt ctattttatt acaaaaggac ggcgtcatca  11160
tggttaagaa agtttttatt atggatagcg taaagacaat aattggtacg ttgcttatag  11220
ctttaggatt acaattttta gcttatccaa ttattaatca acgagtaggt aatgaagcgt  11280
ttggttctat tttaacgatt tatacaataa taacaatcac gagtgttgta ttaggcaata  11340
cgcttaacaa tatacgatta attaatatga atctatacaa atccaatcat tactactgga  11400
aatttgtgtc gatactttta atttcaattc tgattgagag tatagcttta attattgtat  11460
ttctttactt ttttaatttg aacaccatcg atattatctt tttaattcta cttaatattt  11520
taatgtgttt aaggatttat ctgaatgtat tttttaggat gactttaaaa tataatcaga  11580
ttttgtatat tgctcttatt caatttttag gtttgctgat aggactattt ctatattatt  11640
taatccaaaa ctggattgtt tgttttatta ccagtgaatt gtttgcaacg atatatacat  11700
tggttaaatt acggggatta actataggcg agtatcaaag tgaagataat aatgtggtca  11760
aagattatgt gatgctactg agtacaaata gccttaataa tttgaatctc tacttagata  11820
gattaatctt attaccaatt ataggtggaa cagctgtaac tatatcattt ctttcaacat  11880
ttattgggaa aatgttagct acatttctgt atccgattaa taatgtagta ctttcatata  11940
tttctgtaaa tgaaagcgac aatataaaga agcaatattt gaaaactaat ctatttgcta  12000
tagctgcact atgtttagtc atgattatat gttatccaat tacattaatt attgtctctt  12060
tactgtataa cattgattca agtttatatt cgaagtttat tattttaggt aatataggtg  12120
ttttattcaa tgcagtgagt attatgatcc aaactttaaa tacaaaacac gcatcaataa  12180
cattacaagc gaattatatg acgcttcaca cgattacatt tatattcata actattttaa  12240
tgacaattgc gtttggtcta aatggattct tttggacaac gctgttcagc aacattatta  12300
agtatgtgat tttaaatatt ataggtttaa agtctaaatt cattaataaa aaggacgtcg  12360
attagatgag tgaaaaaaag attttgattt tatgtcagta tttttatccg gaatatgtat  12420
cttctgcgac gttaccaact caattggcgg aagatttaat tgcgaatcac attaatgtcg  12480
atgtcatgtg tggatggcca tatgaatata gtaatcataa acaggtttct aaaaccgaga  12540
tgcatcgtgg aattcgcatt cgacgtctca agtattcgag gtttaataac aaaagtaagg  12600
ttggaaggat catcaatttc tttagtttat tttcaaaatt cgtgattaat atacctaaaa  12660
tgttgaaata tgatcagatt cttgtttact ctaatccacc aatcttgcca ttaataccag  12720
acgttttaca cagactgctt aagaaaaaat attcttttgt ggtgtatgat atagcacctg  12780
ataatgcgat taagacaggt gcaactcgtc caggtagcat gattgataag ctgatgcgtt  12840
acattaatag acatgtctac aagaatgctg aaaatgtcat tgtccttggt acggaaatga  12900
aaaactactt actaaatcat caaatttcta aaaatgctga caatatccat gtgattccta  12960
actggtatga catgcgtcaa ttacaagaca atcgtatcta taatgacaca tttaaagctt  13020
accgtgagca atacgacaaa attttattgt atagcggtaa tatggggcag ttacaggata  13080
tggagacact tatctcattt ttaaaattaa ataaggatca gcctcaaacg ttaacaatac  13140
tttgtggtca tggtaagaaa tttgcagatg tcaaaacggc aatagaagac catcgtattg  13200
```

-continued

```
aaaatgttaa aatgtttgag tttttaacag gtacagacta tgctgacgta ttaaaaattg  13260
cggatgtatg tattgcatcg ctgattaaag aaggcgtcgg tttaggcgtt ccgagcaaga  13320
attatggcta ccttgcagct aagaaaccgt tggtactcat catggataag caatctgata  13380
tcgttcaaca tgttgaacaa tatgatgcgg gtatccaaat tgataatggc gatgcacatg  13440
ccatttataa cttcatcaac actcactcga gtaaggaatt gcacgagatg ggtgagcgcg  13500
cacatcaact gtttaaagat aaatatacga gagaaattaa tactatgaag tattacaatc  13560
tgttgaagtg aggagataat tatgaagcga ttattcgatg tagtgagttc aatatatggt  13620
ttagtagttt taagtccgat tctgttaatt acagcattac taattaaaat ggaatcacct  13680
ggaccagcca ttttcaaaca aaaaagaccg acgattaata atgaattgtt taatatttat  13740
aagtttagat caatgaaaat agacacacct aatgttgcaa ctgatttaat ggattcaaca  13800
tcgtatataa caaagacagg gaaggtcatt cgtaagacct ctattgatga attgccacaa  13860
ttattgaatg ttttaaaagg agaaatgtca attgtaggtc ctagaccagc gctttataat  13920
caatacgaat taatcgaaaa acgtacaaaa gcgaacgtgc atacgattag accaggtgtg  13980
acaggactag ctcaagtgat ggggagagat gatattactg atgatcaaaa agtagcgtat  14040
gatcattatt acttaacaca tcaatctatg atgcttgata tgtatatcat atataaaaca  14100
attaaaaata tcgttacttc agaaggtgtg catcactaat gagaaaaaat attttaatta  14160
caggcgtaca tggatatatc ggtaatgctt taaaagataa gcttattgaa caaggacatc  14220
aagtagatca aattaatgtt aggaatcaat tatggaagtc gacctcgttc aaagattatg  14280
atgttttaat tcatacagca gctttggttc acaacaattc acctcaagca aggctatctg  14340
attatatgca agtgaatatg ttgcttacga aacaattggc acaaaaggct aaagctgaag  14400
acgttaaaca atttattttt atgagtacta tggcagttta tggaaaagaa ggtcaggttg  14460
gtaaatcaga tcaaattgat acacaaacac caatgaaccc tacgaccaac tatggtattt  14520
ccaaaaagtt cgctgaacaa gcattacaag agttgattag tgattcgttt aaagtagcaa  14580
ttgtgagacc accaatgatt tatggtgcac attgcccagg aaatttccaa cggttaatgc  14640
aattgtcaaa gcgactgcca atcattccca atattaacaa tcagcgcagt gcattatata  14700
ttaaacatct gacagcattt attgatcaat taatatcatt agaagtgaca ggcgtgtatc  14760
atcctcaaga tagtttttac tttgatacat cgtcagtaat gtatgaaata cgtcgccaat  14820
cacatcgtaa aacggtattg atcaacatgc cttcagtgtt aaataagtat tttaataagt  14880
tgtcggtctt tagaaaatta ttcggcaatt taacatacag caatacgtta tatgaaaata  14940
ataatgcact tgaagttatt cctggaaaaa tgtcacttgt tattgcggac atcatggatg  15000
aaacgacaac caaagataag gcataagtca tctattaaat aaaatcaaca tacaaatcgt  15060
tttatttgga ggttatagta tgaagttaac agtagttggc ttaggttata ttggtttacc  15120
aacatcaatt atgtttgcaa agcatggcgt cgatgtgctt ggtgttgata ttaatcagca  15180
aacgattgat aagttacaaa gtggtcaaat tagtattgaa gaacctgggt tacaagaggt  15240
ttatgaagag gtactgtcat cgggaaaatt gaaggtatct acaacgccag aagcatctga  15300
tgtttttatc attgccgttc cgacgccgaa taatgatgat cagtaccggt catgtgacat  15360
ttcgctagtt atgcgtgcat tagatagtat tttaccattt ttagaaaaag ggaatactat  15420
tattgtagag tcgacaattg cgcctaaaac gatggatgat tttgtaaaac cagtcattga  15480
aaatttagga tttacaatag gtgaagatat ttgtttagtg cattgtccag aacgtgtact  15540
gccaggaaaa attttagaag aattagttca taacaatcgt atcattggcg gtgtgactaa  15600
```

agcttgtatt gaagcgggta aatatgtcta tcgcacattc gttcagggag aaatgattga 15660
aacagatgca cgtactgctg aaatgagtaa gctaatggaa aacacatata gagacgtgaa 15720
tattgcttta gctaatgaat taacaaaaat ttgcaataac ttaaatatta atgtattaga 15780
tgtgattgaa atggcaaaca aacatccgcg tgttaatatc catcaacctg gtccaggtgt 15840
aggcggtcat tgtttagctg ttgatccgta ctttattatt gctaaagacc ctgaaaatgc 15900
aaagttaatt caaactggac gtgaaattaa taattcaatg ccggcctatg ttgttgatac 15960
aacgaagcaa atcatcaaag cgttgagcgg gaataaagtc acagtatttg gtttaactta 16020
taaaggtgat gttgatgata taagagaatc gccagcattt gatatttatg agctattaaa 16080
tcaagaacca gacatagaag tatgtgctta tgatccacat gttgaattag attttgtgga 16140
acatgatatg tcacatgctg tcaaagacgc atcgctagta ttgattttaa gtgaccactc 16200
agaatttaaa aatttatcgg acagtcattt tgataaaatg aagcataaag tgatttttga 16260
tacaaaaaat gttgtgaaat catcatttga agatgtatcg tattataatt atggcaatat 16320
atttaatttt atcgacaaat aaaatgtgtc aaactagggc atacatgatt aaggaaagat 16380
aagctgtcat gtgtttgaac ttcagagagg ataatgttat gaaaaaaatt atggttattt 16440
tcggtacgag acccgaagca ataaaaatgg caccattagt aaaagaaatt gatcataatg 16500
ggaactttga agcgaacatt gtgattacag cacaacatag agatatgtta gatagtgtgt 16560
taagtatatt tgatattcaa gctgatcatg atttaaatat tatgcaagat caacaaacgt 16620
tagcggacct tacggcgaat gcgcttgcta aacttgatag catcattaat gaggaacagc 16680
cggatatgat tttagtacat ggtgatacta caacgacttt tgtaggaagt ttggcagcat 16740
tttatcatca aattccggtt ggacatgtag aagctggact tcgaacacat cagaaatact 16800
caccatttcc tgaagagtta aatcgagtca tggtaagtaa tattgctgaa ttgaattttg 16860
cgccaacagt aattgcagct aaaaatttac tttttgaaaa caaagacaaa gagcgtatct 16920
ttattactgg aaatacagtt attgacgcat tgtcaacaac agttcaaaat gattttgttt 16980
caacgattat taataaacat aaaggcaaga aagttatttt actaacagcg catcgtcgtg 17040
aaaatattgg ggaaccgatg catcagattt ttaaagcagt aagagatttg gcagatgaat 17100
ataaagatgt tgtcttcatt tatccaatgc atcgtaatcc aaaggtaaga gcgattgccg 17160
aaaaatattt atctgggaga aatcggattg aattaattga gccattagat gcgattgagt 17220
tccataattt tacaaatcaa tcgtacctcg tgctgacaga ttctggtggt attcaagagg 17280
aggctcctac atttggaaaa cctgtgttgg tattaaggaa tcatacagag cgtcccgaag 17340
gcgttgaggc gggaacatcg agagtaattg gcacagatta tgacaatatt gttcgaaatg 17400
tgaaacaatt gattgaggat gatgaagcgt atcaacgtat gagtcaagcg aataatccat 17460
atggtgatgg acaagcatca cgacgtattt gtgaagcaat agaatattat tttggattgc 17520
gctcagacaa gccggatgaa ttcgtacctt tacgtcacaa ataata 17566

<210> SEQ ID NO 7
<211> LENGTH: 16342
<212> TYPE: DNA
<213> ORGANISM: Staphylococcus aureus

<400> SEQUENCE: 7
gagtctacaa gcgattaaat tgacgttcga atatttaaaa tcatctgttg aaaagggtga 60
taaagtttca agagagaaaa tgcataacgc atcaactttg gctggtatgg catttgcaaa 120
tgcattctta ggcattgcac actcaattgc acataaaatt ggtggcgaat atggtattcc 180

-continued

```
gcatggtaga gcgaatgcga tattactacc gcatattatc cgttataatg ccaaagaccc    240
gcaaaaacat gcattattcc ctaaatatga gttcttcaga gcagatacag attatgcaga    300
tattgccaaa ttcttaggat taaaagggaa tacgacagaa gcactcgtag aatcattagc    360
taaagctgtc tacgaattag gtcaatcagt cggaattgaa atgaatttga aatcacaagg    420
tgtgtctgaa gaagaattaa atgaatcaat tgatagaatg gcagagctcg catttgaaga    480
tcaatgtaca actgctaatc ctaaagaagc actaatcagt gaaatcaaag atatcattca    540
aacatcatat gattataagc aataatctat ctgataataa tcatataact cacctgaaat    600
tacaaaagta aaaaatgcca cataaacttt aagtcgataa tcatttttacg gttatcggct    660
tttatttatt gccaaatctt cagagataca aactagacaa tcattttttt aaataaagaa    720
aatattaaga ttgatactca tttcgcaaac tattactact ttagagccat ggccacagta    780
taaattatat cagtatgctt atataatttt tgaaatcttt aaacaaatga agtaataatt    840
gagaaaagtg tagttaaatt atttttcttg aaattatttg ttacatagca tttcgatgta    900
aaattcactt tttataagta aatttaaaaa gagtttgcaa aatatacagg ggattatata    960
taatggaaaa caagaaagga aaataggagg tttatatgga aagtacatta gaattaacaa   1020
aaattaaaga agtattacaa aaaaacttga agattttaat tattttaccg ctattatttt   1080
taattattag cgctattgtt acatttttcg tcttatcacc taaatatcaa gctaatactc   1140
aaatcttagt gaatcaaact aagggtgaca atcctcagtt tatggcacaa gaggttcaaa   1200
gtaatattca acttgtaaat acgtataaag aaattgttaa aagtcctaga attttagatg   1260
aggtgtcaaa ggacttaaat gataagtatt caccatctaa attgtcgagt atgttgacaa   1320
ttacaaacca agaaaatacg caacttatca acatccaagt taaaagtggt cataaacaag   1380
attcggaaaa aattgcgaat agcttcgcta aagttacaag taaacaaatt ccgaagatta   1440
tgagtgtgga taacgtatca attttatcta aagcagacgg tacagcagtt aaagtcgcac   1500
caaaaactgt agtgaatcta atcggtgcat tctttttagg attagttgtc gcgcttatat   1560
atatcttctt caaagtaatt ttcgataagc gaattaaaga tgaagaagat gtagagaaag   1620
aattaggatt gcctgtattg ggttcaattc aaaaatttaa ttaaggatgg ttgctactta   1680
tgtcaaaaaa ggaaaatacg acaacaacac tatttgtata tgaaaaacca aaatcaacaa   1740
ttagtgaaaa gtttcgaggt atacgttcaa acatcatgtt ttcaaaagca aatggtgaag   1800
taaagcgctt attggttact tctgaaaagc ctggtgcagg taaaagtaca gttgtatcga   1860
atgtagcgat tacttatgca caagcaggct ataagacatt agttattgat ggcgatatgc   1920
gtaagccaac acaaaactat atttttaatg agcaaaataa taatggacta tcaagcttaa   1980
tcattggtcg aacgactatg tcagaagcaa ttacgtcgac agaaattgaa aatttagatt   2040
tgctaacagc tggccctgta cctccaaatc catctgagtt aattgggtct gaaaggttca   2100
aagaattagt tgatctgttt aataaacgtt acgacattat tattgtcgat acaccgccag   2160
ttaatactgt gactgatgca caactatatg cgcgtgctat taaagatagt ctgttagtaa   2220
ttgatagtga aaaaaatgat aaaaatgaag ttaaaaaagc aaaagcactt atggaaaaag   2280
caggcagtaa cattctaggt gtcattttga acaagacaaa ggtcgataaa tcttctagtt   2340
attatcacta ttatggagat gaataagtat gattgatatt cataaccata tattgcctaa   2400
tatcgatgac ggtccgacaa atgaaacaga gatgatggat cttttaaaac aagcgacaac   2460
acaaggtgtt acagaaatca ttgtaacatc acatcactta catcctcgat ataccacacc   2520
tatagaaaaa gtgaaatcat gtttaaacca tattgaaagc ttagaggaag tacaagcact   2580
```

-continued

```
aaatctaaag ttttattatg gtcaggaaat aagaattacc gatcaaatcc ttaatgatat   2640
tgatcgaaaa gttattaccg gtattaatga ttcacgctat ttactaatag aatttccatc   2700
aaatgaagtt ccacactata ctgatcaatt atttttcgaa ttacagagta aaggctttgt   2760
accgattatt gcacatccag agcgaaataa agcaataagt caaaaccttg acatactata   2820
cgatttaatt aacaaaggtg ctttaagtca agtgacaacg gcgtcattag cgggtatttc   2880
cggtaaaaaa attagaaaat tagcaattca aatgattgaa aacaatctga cacatttcat   2940
cggttcagat gcgcataaca cagaaatcag accgttctta atgaaagact tatttaatga   3000
taagaaatta cgtgattatt atgaagatat gaacggattt attagtaatg cgaagttagt   3060
tgttgatgat aaaaaaattc ctaaacgaat gccacaacaa gattataaac agaaaagatg   3120
gtttgggtta taaacagcaa atgaggggtt ttatggcaca tttatctgtg aaattgcggc   3180
ttttaatact agcattaatc gattcactga tagtgacatt ttcagtattc gtaagttatt   3240
acattttaga accgtatttc aaaacatatt ctgtcaaatt attaatattg gcagctatat   3300
cactattcat atcgcatcat atttcagcat ttattttttaa tatgtatcat cgagcgtggg   3360
aatatgccag tgtgagtgaa ttgattttaa ttgttaaagc tgtgacgaca tctatcgtta   3420
ttacgatggt ggtcgtgaca attgttacag gcaatagacc gttttttaga ttgtatttaa   3480
ttacttggat gatgcacttg attttaatag gtggctcaag gttattttgg cgtatttatc   3540
ggaaatacct tggaggtaag tcatttaata agaagccaac tttagttgtt ggtgctggtc   3600
aagcaggttc aatgctgatt agacaaatgt tgaaaagtga cgaaatgaaa cttgaaccgg   3660
tattagcagt cgatgatgac gaacataaac gcaatatcac aattactgag ggtgtaaaag   3720
tccaaggtaa aattgcggat attccagaac tagtgaggaa atataagatt aaaaaaatca   3780
tcattgcaat tccaactatt ggtcaagagc gtttgaaaga aattaataat atttgccata   3840
tggatggcgt tgagttattg aaaatgccaa atatagaaga cgtcatgtct ggtgagttag   3900
aagtgaatca actgaaaaaa gttgaagtag aagatttact aggcagagat cctgttgaat   3960
tagatatgga tatgatatca aatgaattga cgaataaaac tattttagtt acgggtgcag   4020
gtggttcaat aggatcagaa atttgtagac aagtttgtaa tttctatcca gaacgtatta   4080
ttctacttgg ccatggtgaa aacagtattt atttaatcaa tcgtgaattg cgaaatcgct   4140
tcggaaaaaa tgttgatatc gttcctatta tagcggatgt gcaaaataga gcgcgtatgt   4200
ttgaaattat ggaaacgtat aaaccatacg cagtttatca tgcagcagca cacaagcacg   4260
tgccgttaat ggaagacaac cctgaagaag cagtacataa taatatttta ggtacgaaaa   4320
atactgctga agctgctaaa aatgcagagg taaagaaatt cgttatgatt tctacggata   4380
aagccgttaa tccgcctaat gtcatgggag cttcaaagcg aattgcagaa atgattattc   4440
aaagtttaaa tgatgaaacg catcgaacaa attttgttgc agtgagattt ggtaatgtac   4500
ttggatcgag aggatctgtg attccacttt tcaaaagtca aattgaagaa ggtgggccag   4560
ttactgtgac acatcctgaa atgacacgtt actttatgac aattcctgaa gcttctagac   4620
tagttttgca ggcaggggca ttagcagaag gtggcgaagt atttgtgcta gatatgggag   4680
aaccagtgaa aattgtagat ttggcacgta atttaattaa gctaagtggt aaaaaagaag   4740
acgacatacg cattacttat acagggatta gacccggcga aaaaatgttt gaagagctta   4800
tgaataaaga tgaggttcat cctgaacaag tatttgaaaa aatttatcgt ggcaaagtac   4860
aacatatgaa atgtaatgaa gttgaagcga ttattcaaga catcgtcaat gactttagta   4920
aagaaaaaat tattaactat gccaatggca aaaagggaga taattatgtt cgatgacaaa   4980
```

-continued

```
attttattaa ttactggggg cacaggatca ttcggtaatg ctgttatgaa acggttttta   5040
gattctaata ttaaagaaat tcgtattttt tcacgcgatg agaaaaaaca agatgacatt   5100
cgaaaaaaat ataataattc aaaattaaag ttctacattg gtgatgtgcg tgatagtcaa   5160
agtgtagaaa cagcaatgcg agatgttgat tacgtattcc atgcagcagc tttaaaacaa   5220
gtgccgtcat gtgaattctt tccagttgag gcagtgaaga caaatattat tggtacagaa   5280
aatgtcttac aaagtgctat tcatcaaaat gttaaaaaag tcatatgttt atctacagat   5340
aaggcagcgt atcctattaa tgctatgggt atttcaaaag caatgatgga aaaagtattc   5400
gtagccaaat caagaaatat tcgtagtgaa caaacgctta tttgtggtac aagatacggt   5460
aatgtgatgg cttcaagagg atcagtaata cctttgttta tcgacaaaat caaagctgga   5520
gaacctttaa cgattacaga tcctgatatg acaagatttt taatgagctt agaagatgcg   5580
gtagaactag ttgttcatgc atttaagcat gcagagacag gagatattat ggttcaaaaa   5640
gcaccaagct caacggtagg ggatcttgcg accgcattat tagaattgtt tgaagctgat   5700
aatgcaattg aaatcattgg tacgcgacat ggagagaaaa aagcagaaac attgttgacg   5760
agagaagaat acgcacaatg tgaagatatg ggtgattatt ttagagtgcc ggcagactcc   5820
agagatttaa attatagtaa ttatgttgaa accggtaacg aaaagattac gcaatcttat   5880
gaatataact ccgataatac acatatttta acggtggaag agataaaaga aaaacttttta   5940
acactagaat atgttagaaa cgaattgaat gattataaag cttcaatgag ataggagaga   6000
ttgacgttga atattgtaat tacaggagca aaaggttttg taggaaaaaa cttgaaagca   6060
gatttaacat caacgacaga tcatcatatt ttcgaagtac atcgacaaac taaagaggaa   6120
gaattagagt cagcattgtt gaaagcagac tttatcgtgc atttagcggg tgttaatcga   6180
cctgaacatg acaaagaatt cagcttagga aacgtgagtt atttagatca tgtacttgat   6240
atattaacta gaaatacgaa aaagccagcg atattattat cgtcttcaat acaagcaaca   6300
caagataatc cttatggtga gagtaagttg caaggggaac agctattaag agagtatgcc   6360
gaagagtatg gcaatacggt ttatatttat cgctggccaa atttattcgg caagtggtgt   6420
aagccgaatt ataactcagt gatagcaaca ttttgttaca aaattgcacg taacgaagag   6480
attcaagtta atgatcggaa tgttgaacta acgctaaact acgtggatga tatcgtcgct   6540
gaaataaagc gtgctattga aggaactcca acgattgaaa atggtgtacc tacagtacca   6600
aacgtattta aagtgacatt gggagaaatt gtagatttat tatacaagtt caaacagtca   6660
cgtctcgatc gaacattgcc gaaattagat aacttgtttg aaaaagattt gtatagtacg   6720
tatttaagct atctacctag tacagacttt agttatccct tacttatgaa tgtggatgat   6780
aggggttctt ttacagaatt tataaaaaca ccggatcgtg gtcaagtttc tgtaaatatt   6840
tctaaaccag gtattactaa aggtaatcac tggcaccata ctaaaaacga aaaatttcta   6900
gtcgtatcag gtaaaggggt aattcgtttt agacatgtta atgatgatga aatcattgaa   6960
tattacgttt ctggcgataa attagaagtt gtagacatac cagtaggata cacacataat   7020
attgaaaatt taggcgacac agatatggta actattatgt gggtgaatga aatgtttgat   7080
ccaaatcagc cagatacgta tttcttggag gtatagcgca tggaaaaact gaaattaatg   7140
acaatagttg gtacaaggcc tgaaatcatt cgtttatcat caacgattaa agcatgtgat   7200
caatatttta atcagatatt agtacacact ggtcaaaatt atgattatac attgaatcaa   7260
attttctttg atgatttgga attaagacaa ccggaccact acttagaggc agttggaagt   7320
aaccttggag aaacgatggg gaatattatt gcgaagacat atgacgtttt attacgcgaa   7380
```

-continued caaccagatg cacttttaat tcttggtgat acaaatagtt gtttagcagc agtatctgct 7440
aaacgattaa agattcctgt gttccacatg gaagcgggta atagatgctt tgatcagaat 7500
gtacctgaag aaatcaatcg taaaattgtt gaccatgtca gtgatgtgaa tctaccttat 7560
acagaacata gcagacggta tttattagat gaaggcttca ataaagcgaa tatctttgtg 7620
acaggatcac cgatgacaga agtgatagaa gcgcatcgag ataaaattaa tcacagtgac 7680
gttttaaata aactaggatt agaaccgcaa caatacattt tagtatctgc gcatagagaa 7740
gagaatatcg ataatgaaaa gaattttaaa tcattaatga atgcgataaa tgatattgcc 7800
aaaaagtata aaatgcctgt gatttattca acgcatccaa gaagttggaa gaaaattgaa 7860
gaaagtaaat ttgaatttga tccattagtt aaacagttaa agccatttgg tttctttgat 7920
tataatgcat tgcaaaaaga tgcatttgtt gtgctatcag atagtggaac attgtcagaa 7980
gagtcgtcta ttttgaagtt ccctggtgtc cttattcgaa cttccacaga aagaccggaa 8040
gtactagata aaggtacggt tattgtaggt ggtattacct ataacaatct aatccaatcc 8100
gttgaactag caagagagat gcaaaacaat aacgaaccga tgattgatgc tattgattat 8160
aaagacacta acgtttcgac aaaggtagtt aaaattattc aaagctataa agatattatc 8220
aatcgaaata cttggaggaa atgacgatga ggatagcgat tgaaaagata attggtttgc 8280
tgaaaaacca gtcctctaaa gaatcgaatg ttaagattca tcgcttggcg tatattacaa 8340
actcaaaatt tgatggcaat aactatatag atagatggtg taaaatcagg aattctcaca 8400
ttggtgaata cagttatatt ggatttggta gtgattttaa taatgtagaa gtaggaagat 8460
attgttcgat atcttcggat gtaaaaattg ggttaggaaa acatcctaca cacttttta 8520
gctcatcacc gatttttat tctaataata atccatttaa cataaagcaa aagtttatag 8580
actttaatga ccaaccaagc cgtacaacaa ttaaaaatga tgtgtggatt ggtgcaaatg 8640
taattattat ggatggatta acaataaata ctggtgcagt catagcagcc ggctcagttg 8700
ttactaaaaa tgtaggagca tatgaggttg ttggtggggt tcctgcaaaa gtgattaaga 8760
agcgatttga caataaaaca attgaaaaac ttttggaaag caagtggtgg gagaaaacgc 8820
ctgacaaact aaaaggattt tcggttgaat atttaaataa aaaggatact taatgatatg 8880
agaattttaa atattgtatc gagtaatatt gttcaagacc caagggtact taaacaaata 8940
gaaacaatta aaggcgttac gaatgattat aaaattgttg gaatgaataa ttcacaagct 9000
actaataggc gattggaaaa tttagattgt aattatcgtt tgttaggtag caaggtagat 9060
cccaaaaata ttctttctaa attaattaag cgtataagat ttgcaacagg tgttatccga 9120
gaaattaaag cttttaaacc tgacgtgatt catgcaaatg atttcgacgt attattaatg 9180
gtctatttaa gcaattataa aaaagctaat attgtttatg atgcgcatga aatatatgcg 9240
aaaaatgcct ttattaataa agttccactt atttcaaagt ttgtagaaag tatagaaaaa 9300
cacatagtaa aacatcgtgt taatgccttc gtaacagtaa gtcatgcagc aaaagaatat 9360
tatcaatcta aaggatataa gaaggaagcg aatgttatta cgaatgcacc tattttaaat 9420
gatagcagag aatttaaaga aatcgaaaac tttaaagaaa tcgtatatca aggtcaaatt 9480
gtaatggaca gaggatatga agagtttatt attgcttcat cagcttttaa acaaaatgct 9540
ccttcattca taattcgagg gtttggtccg catgaagaag tgataaaaga actgattagt 9600
tataactcgg aaaatattag gttggataaa ccagttgaag taaaagaatt ggttgataag 9660
ttagcagaaa gtaatgttgg tgttatcttg acgaaacctg tatctattaa ttttgaatat 9720
acagtatcta ataaaatttt tgaatgtata catgctggtt taccagtaat tttatctcct 9780

-continued

```
gtcaaagagc atatttatct caatgaaaaa tataaatttg gcattgtttt aaaggaagtt   9840
acgccgttag aaattgaaaa ggcggttaga aaattaagag ataatcacga tttgtttaat   9900
catttacgtc aaaatgcaat taaggcgtct aaaattttga attggcaaat agaaagtgaa   9960
cgattagtag aattatataa attttaaaga gaggtaaact atgaaatttt ttgtactttg  10020
tgcaattatc agcatgaaca tatttatagt aatctctaca tttactaaag aagtattagg  10080
gttccctata gagccggtgt attactcaac catggttggt atagcattaa ttactacggt  10140
gtttgctatt tataagataa ttgtcacgca agaaattccg cgagggttaa tattattaat  10200
tgctatatgt ttgctttatc tagcttttta ttatttttca ccagataagg aagagaaact  10260
agctaaaaat aatattctat tctttttaac atgggcagtt ccagcggcaa ttagtggtat  10320
ttatattaaa tatataaaca aggctacggt agaaagattt tttaaattag tatttttcat  10380
attttctatt tcatttattt ttgtaatttt aataccaaaa cttacaggtg agatacctag  10440
ctatatcaat tttggactta tgaactatca aaacgcttcg tacctttcag catttactgc  10500
cggattaggc atttatttca ttatgaaagg ttcagtgaaa cataagtgga tatatgttct  10560
atttacaata attgatatcc ctattgtgtt tataccagga gggcgtggag gtgctatttt  10620
attaattctt tacggcttat ttgcatttat acttattacg tttaaaagag gaatacctat  10680
tgcagtaaaa agcattatgt atatttttgc attaagcata tctagtgtat tgatttactt  10740
tctttttaca aaaggttcga atactagaac attttcatat ctacaaggtg gaacacttaa  10800
tttagaaggt acttctggaa gaggaccgat ttatgaaaaa ggtatttact ttattcaaca  10860
aagtccgtta ttaggctatg ggccatttaa ctattataaa ctaatcggaa atataccaca  10920
taacatcatt attgagttga ttctatcatt tggcttatta gggtttttta tcataatgat  10980
ttgcattttg ctactagttt ataaaatgat taggaactat gatccaaaca ctatagattt  11040
actcgttatg tttatagcaa tctatccaat cacattatta atgtttagtt caaattattt  11100
agttgtaagt gaattttggt ttgtgttgtt ctattttatt acaaaaggac ggcgtcatca  11160
tggttaagaa agtttttatt atggatagcg taaagacaat aattggtacg ttgcttatag  11220
ctttaggatt acaattttta gcttatccaa ttattaatca acgagtaggt aatgaagcgt  11280
ttggttctat tttaacgatt tatacaataa taacaatcac gagtgttgta ttaggcaata  11340
cgcttaacaa tatacgatta attaatatga atctatacaa atccaatcat tactactgga  11400
aatttgtgtc gatactttta atttcaattc tgattgagag tatagcttta attattgtat  11460
ttctttactt ttttaatttg aacaccatcg atattatctt tttaattcta cttaatattt  11520
taatgtgttt aaggatttat ctgaatgtat tttttaggat gactttaaaa tataatcaga  11580
ttttgtatat tgctcttatt caatttttag gtttgctgat aggactattt ctatattatt  11640
taatccaaaa ctggattgtt tgttttatta ccagtgaatt gtttgcaacg atatatacat  11700
tggttaaatt acggggatta actataggcg agtatcaaag tgaagataat aatgtggtca  11760
aagattatgt gatgctactg agtacaaata gccttaataa tttgaatctc tacttagata  11820
gattaatctt attaccaatt ataggtggaa cagctgtaac tatatcattt ctttcaacat  11880
ttattgggaa aatgttagct acatttctgt atccgattaa taatgtagta ctttcatata  11940
tttctgtaaa tgaaagcgac aatataaaga agcaatattt gaaaactaat ctatttgcta  12000
tagctgcact atgtttagtc atgattatat gttatccaat tacattaatt attgtctctt  12060
tactgtataa cattgattca agtttatatt cgaagtttat tattttaggt aatataggtg  12120
ttttattcaa tgcagtgagt attatgatcc aaactttaaa tacaaaacac gcatcaataa  12180
```

cattacaagc gaattatatg acgcttcaca cgattacatt tatattcata actattttaa 12240
tgacaattgc gtttggtcta aatggattct tttggacaac gctgttcagc aacattatta 12300
agtatgtgat tttaaatatt ataggtttaa agtctaaatt cattaataaa aaggacgtcg 12360
attagatgag tgaaaaaaag attttgattt tatgtcagta tttttatccg gaatatgtat 12420
cttctgcgac gttaccaact caattggcgg aagatttaat tgcgaatcac attaatgtcg 12480
atgtcatgtg tggatggcca tatgaatata gtaatcataa acaggtttct aaaaccgaga 12540
tgcatcgtgg aattcgcatt cgacgtctca agtattcgag gtttaataac aaaagtaagg 12600
ttggaaggat catcaatttc tttagtttat tttcaaaatt cgtgattaat atacctaaaa 12660
tgttgaaata tgatcagatt cttgtttact ctaatccacc aatcttgcca ttaataccag 12720
acgttttaca cagactgctt aagaaaaaat attcttttgt ggtgtatgat atagcacctg 12780
ataatgcgat taagacaggt gcaactcgtc caggtagcat gattgataag ctgatgcgtt 12840
acattaatag acatgtctac aagaatgctg aaaatgtcat tgtccttggt acggaaatga 12900
aaaactactt actaaatcat caaatttcta aaaatgctga caatatccat gtgattccta 12960
actggtatga catgcgtcaa ttacaagaca atcgtatcta taatgacaca tttaaagctt 13020
accgtgagca atacgacaaa attttattgt atagcggtaa tatggggcag ttacaggata 13080
tggagacact tatctcattt ttaaaattaa ataaggatca gcctcaaacg ttaacaatac 13140
tttgtggtca tggtaagaaa tttgcagatg tcaaaacggc aatagaagac catcgtattg 13200
aaaatgttaa aatgtttgag tttttaacag gtacagacta tgctgacgta ttaaaaattg 13260
cggatgtatg tattgcatcg ctgattaaag aaggcgtcgg tttaggcgtt ccgagcaaga 13320
attatggcta ccttgcagct aagaaaccgt tggtactcat catggataag caatctgata 13380
tcgttcaaca tgttgaacaa tatgatgcgg gtatccaaat tgataatggc gatgcacatg 13440
ccatttataa cttcatcaac actcactcga gtaaggaatt gcacgagatg ggtgagcgcg 13500
cacatcaact gtttaaagat aaatatacga gagaaattaa tactatgaag tattacaatc 13560
tgttgaagtg aggagataat tatgaagcga ttattcgatg tagtgagttc aatatatggt 13620
ttagtagttt taagtccgat tctgttaatt acagcattac taattaaaat ggaatcacct 13680
ggaccagcca ttttcaaaca aaaaagaccg acgattaata atgaattgtt taatatttat 13740
aagtttagat caatgaaaat agacacacct aatgttgcaa ctgatttaat ggattcaaca 13800
tcgtatataa caaagacagg gaaggtcatt cgtaagacct ctattgatga attgccacaa 13860
ttattgaatg ttttaaaagg agaaatgtca attgtaggtc ctagaccagc gctttataat 13920
caatacgaat taatcgaaaa acgtacaaaa gcgaacgtgc atacgattag accaggtgtg 13980
acaggactag ctcaagtgat ggggagagat gatattactg atgatcaaaa agtagcgtat 14040
gatcattatt acttaacaca tcaatctatg atgcttgata tgtatatcat atataaaaca 14100
attaaaaata tcgttacttc agaaggtgtg catcactaat gagaaaaaat attttaatta 14160
caggcgtaca tggatatatc ggtaatgctt taaaagataa gcttattgaa caaggacatc 14220
aagtagatca aattaatgtt aggaatcaat tatggaagtc gacctcgttc aaagattatg 14280
atgttttaat tcatacagca gctttggttc acaacaattc acctcaagca aggctatctg 14340
attatatgca agtgaatatg ttgcttacga aacaattggc acaaaaggct aaagctgaag 14400
acgttaaaca atttatttt atgagtacta tggcagttta tggaaaagaa ggtcaggttg 14460
gtaaatcaga tcaaattgat acacaaacac caatgaaccc tacgaccaac tatggtattt 14520
ccaaaaagtt cgctgaacaa gcattacaag agttgattag tgattcgttt aaagtagcaa 14580

-continued

```
ttgtgagacc accaatgatt tatggtgcac attgcccagg aaatttccaa cggttaatgc  14640

aattgtcaaa gcgactgcca atcattccca atattaacaa tcagcgcagt gcattatata  14700

ttaaacatct gacagcattt attgatcaat taatatcatt agaagtgaca ggcgtgtatc  14760

atcctcaaga tagtttttac tttgatacat cgtcagtaat gtatgaaata cgtcgccaat  14820

cacatcgtaa aacggtattg atcaacatgc cttcagtgtt aaataagtat tttaataagt  14880

tgtcggtctt tagaaaatta ttcggcaatt taacatacag caatacgtta tatgaaaata  14940

ataatgcact tgaagttatt cctggaaaaa tgtcacttgt tattgcggac atcatggatg  15000

aaacgacaac caaagataag gcataagtca tctattaaat aaaatcaaca tacaaatcgt  15060

tttatttgga ggttatagta tgaagttaac agtagttggc ttaggttata ttggtttacc  15120

aacatcaatt atgtttgcaa agcatggcgt cgatgtgctt ggtgttgata ttaatcagca  15180

aacgattgat aagttacaaa gtggtcaaat tagtattgaa gaacctgggt tacaagaggt  15240

ttatgaagag gtactgtcat cgggaaaatt gaaggtatct acaacgccag aagcatctga  15300

tgtttttatc attgccgttc cgacgccgaa taatgatgat cagtaccggt catgtgacat  15360

ttcgctagtt atgcgtgcat tagatagtat tttaccattt ttagaaaaag ggaatactat  15420

tattgtagag tcgacaattg cgcctaaaac gatggatgat tttgtaaaac cagtcattga  15480

aaatttagga tttacaatag gtgaagatat ttgtttagtg cattgtccag aacgtgtact  15540

gccaggaaaa attttagaag aattagttca taacaatcgt atcattggcg gtgtgactaa  15600

agcttgtatt gaagcgggta aatatgtcta tcgcacattc gttcagggag aaatgattga  15660

aacagatgca cgtactgctg aaatgagtaa gctaatggaa aacacatata gagacgtgaa  15720

tattgcttta gctaatgaat taacaaaaat ttgcaataac ttaaatatta atgtattaga  15780

tgtgattgaa atggcaaaca aacatccgcg tgttaatatc catcaacctg gtccaggtgt  15840

aggcggtcat tgtttagctg ttgatccgta ctttattatt gctaaagacc ctgaaaatgc  15900

aaagttaatt caaactggac gtgaaattaa taattcaatg ccggcctatg ttgttgatac  15960

aacgaagcaa atcatcaaag cgttgagcgg gaataaagtc acagtatttg gtttaactta  16020

taaaggtgat gttgatgata taagagaatc gccagcattt gatatttatg agctattaaa  16080

tcaagaacca gacatagaag tatgtgctta tgatccacat gttgaattag attttgtgga  16140

acatgatatg tcacatgctg tcaaagacgc atcgctagta ttgattttaa gtgaccactc  16200

agaatttaaa aatttatcgg acagtcattt tgataaaatg aagcataaag tgatttttga  16260

tacaaaaaat gttgtgaaat catcatttga agatgtatcg tattataatt atggcaatat  16320

atttaatttt atcgacaaat aa                                           16342
```

<210> SEQ ID NO 8
<211> LENGTH: 29
<212> TYPE: DNA
<213> ORGANISM: PCR primer

<400> SEQUENCE: 8

```
ggatcccttt tacctgcacc aggcttttc                                       29
```

<210> SEQ ID NO 9
<211> LENGTH: 27
<212> TYPE: DNA
<213> ORGANISM: PCR primer

<400> SEQUENCE: 9

```
ccatggctct aaagtagtaa tagtttg                                         27
```

-continued

```
<210> SEQ ID NO 10
<211> LENGTH: 36
<212> TYPE: DNA
<213> ORGANISM: PCR primer

<400> SEQUENCE: 10

ttctaatgta ctttccatat aaacctccta ttttcc                            36


<210> SEQ ID NO 11
<211> LENGTH: 36
<212> TYPE: DNA
<213> ORGANISM: PCR primer

<400> SEQUENCE: 11

aaataggagg tttatatgga aagtacatta gaatta                            36


<210> SEQ ID NO 12
<211> LENGTH: 25
<212> TYPE: DNA
<213> ORGANISM: PCR primer

<400> SEQUENCE: 12

gaattcgagt ctacaagcga ttaaa                                        25


<210> SEQ ID NO 13
<211> LENGTH: 30
<212> TYPE: DNA
<213> ORGANISM: PCR primer

<400> SEQUENCE: 13

cggccatggc cacagtataa attatatcag                                   30
```